US006579236B2

(12) United States Patent
Pratt

(10) Patent No.: US 6,579,236 B2
(45) Date of Patent: Jun. 17, 2003

(54) RUMINANT TISSUE ANALYSIS AT PACKING PLANTS FOR ELECTRONIC CATTLE MANAGEMENT AND GRADING MEAT

(75) Inventor: William C. Pratt, Canyon, TX (US)

(73) Assignee: Micro Beef Technologies, Ltd., Amarillo, TX (US)

( * ) Notice: Subject to any disclaimer, the term of this patent is extended or adjusted under 35 U.S.C. 154(b) by 0 days.

(21) Appl. No.: 09/802,743

(22) Filed: Mar. 8, 2001

(65) Prior Publication Data

US 2001/0044579 A1 Nov. 22, 2001

Related U.S. Application Data

(63) Continuation of application No. 09/190,916, filed on Nov. 12, 1998, now Pat. No. 6,200,210, which is a continuation-in-part of application No. 08/838,768, filed on Apr. 10, 1997, now Pat. No. 6,000,361, and a continuation-in-part of application No. 08/748,220, filed on Nov. 12, 1996, now Pat. No. 5,836,880.

(51) Int. Cl.$^7$ ................................................. A61B 8/00
(52) U.S. Cl. ..................................................... 600/437
(58) Field of Search ................................ 600/407–408; 452/52–60, 149, 150; 73/625, 626; 119/502, 512, 840, 842; 348/89

(56) References Cited

U.S. PATENT DOCUMENTS

| | | |
|---|---|---|
| 5,673,647 A | 10/1997 | Pratt |
| 5,836,880 A | 11/1998 | Pratt |
| 6,000,361 A | 12/1999 | Pratt |
| 6,135,055 A | 10/2000 | Pratt |
| 6,200,210 B1 * | 3/2001 | Pratt ........................... 452/52 |
| 6,318,289 B1 | 11/2001 | Pratt |

OTHER PUBLICATIONS

"Answer to Request No. 20—List of Patents, Articles, and other prior–art references," Fax Transmission from Mullin, Hoard & Brown to Klarquist Sparkman, 12 pp. (Dec. 2001).
"Articles Received from Future Beef," pp. 1–5.
"Executive Summary National Beef Quality Audit," Published by the National Cattlemen's Association in Coordination with Colorado State University and Texas A&M University, 24 pp. (1992) (month not in issue, year sufficiently early —"the year of publication [without the month] will be accepted if the applicant points out in the information disclosure statement that the year of publication is sufficiently earlier than the effective U.S. filing date and any foreign priority date so that the particular month of publication is not in issue" MPEP 609).

(List continued on next page.)

Primary Examiner—Marvin M. Lateef
Assistant Examiner—Ali M. Imam
(74) Attorney, Agent, or Firm—Klarquist Sparkman, LLP

(57) ABSTRACT

A method is described comprising stunning a ruminant at a packing plant, and thereafter measuring tissue characteristics of the ruminant using a tissue imaging and analysis device prior to processing the ruminant to a carcass. Working embodiments of the method have used an ultrasound tissue imaging and analysis device, although other analyses also can be performed. The method can be used to, amongst other things, measure backfat and rib eye dimensions, obtain an ultrasound image, and determine rib eye area and marbling using the measured tissue characteristics. A method for processing and managing ruminants and ruminant products in feedlots and packing plants also is described comprising first measuring internal tissue characteristics and/or external body dimensions of ruminants at a feedlot. These ruminants are then fed at the feedlot, and then shipped to a packing plant where tissue characteristics of stunned ruminants are measured using a tissue imaging and analysis device.

5 Claims, 13 Drawing Sheets

OTHER PUBLICATIONS

"Nutrient Requirements of Beef Cattle," 7$^{th}$ Edition (1996) (month not in issue, year sufficiently early).
"XIIIth World Congress of Diseases of Cattle," World Buiatrics Association, Proceedings vol. 1 (Sep. 1984).
37$^{th}$ Biennial Report, Kansas Agricultural Experiment Station, Director's Report for the Biennium Jul. 1, 1992 to Jun. 30, 1994, Kansas State University (1995) (month not in issue, year sufficiently early).
38$^{th}$ Biennial Report, Kansas Agricultural Experiment Station, Director's Report for the Biennium Jul. 1, 1994 to Jun. 30, 1996, Kansas State University (1997) (month not in issue, year sufficiently early).
Abdullah et al., "Relationships between objective and subjective measurements of carcass muscularity," Proceedings of the New Zealand Society of Animal Production, vol. 53, pp. 397–402 (1993) (month not in issue, year sufficiently early).
Allen et al., "Relationship of physically separable muscle, fat and bone from the left side of steer carcasses to yields of retail cuts, fat trim and bone of the right side," pp. 311–315 (Circa more than one year prior to Mar. 8, 2001).
Barber et al., "Charolais and angus steers slaughtered at equal percentages of mature cow weight. I. Effects of slaughter weight and diet energy density on carcass traits," pp. 218–230 (Circa more than one year prior Mar. 8, 2001).
Berg and Butterfield, "Muscle: Bone Ratio and Fat Percentages as Measures of Beef Carcass Composition," *Animal Production*, vol., 8, Part 1, pp. 1–11 (Feb. 1996).
Bond et al., "Effects of Feeding Level on Growth, Composition of Gain, Carcass Quality and Mature Body Size in Steers at Ages up to Six Years," *Growth*, pp. 388–403 (1982) (month not in issue, year sufficiently early).
Brethour, "Estimating Marbling Score in Live Cattle from Ultrasound Images Using Pattern Recognition and Neural Network Procedures," [Fort Hays Branch Experiment Station] Kansas State University, Fort Hays Branch Experiment Station (Circa more than one year prior to Nov. 12, 1998).
Busch et al., "Body Measurements, Subjective Scores and Estimates of Certain Carcass Traits as Predictors of Edible Portion in Beef Cattle," pp. 557–556 (Circa more than one year prior to Nov. 12, 1998).
Butcher and Webb, "Equipment for Farm Use in the National Cooperative Dairy Herd Improvement Program," National Cooperative Dairy Herd Improvement Program Handbood (1985) (month not in issue, year sufficiently early).
Clayton, "Prediction of Feedlot Characteristics and Carcass Characteristics Using Feeder Cattle Traits," Thesis, Colorado State University (1982) (month not in issue, year sufficiently early).
Corah et al., "Feeding Your Cows by Body Condition", November Kansas State University [Agricultural Experiment Station and Cooperative Extension Services] (1991) (month not in issue, year sufficiently early).
Cornett, "Sorting By Computer Eye: System measures body so arrivals can be grouped to hit carcass specs." *Beef*, pp. 74–78 (Apr. 1994).
Cundif et al., "Breeding Cattle for Improved Product Consistency," Roman L. Hurska US Meat Animal Research Center, Clay Center, Nebraska, pp. 1–28 (1994) (month not in issue, year sufficiently early).
CVP Withdrawal Time Charts (Circa more than one year prior to Nov. 12, 1998).

Daley, "Prediction of Beef Carcass Composition Using Preslaughter Linear Measures," Thesis, Colorado State University (1981) (month not in issue, year sufficiently early).
Daley, "Relationship of Pre–weaning Measures and Performance Traits in Beef Cattle," Dissertation, Colorado State University (1984) (month not in issue, year sufficiently early).
Deterling, "It's What's Under the Hide That Counts," *Progressive Farmer*, pp. 62–63 (Feb. 1995).
Doye and Northcutt, "Integrated Resource Management (IRM) Tools: Standard Performance Analysis Cow–Calf Software," Oklahoma Cooperative Extension Service, Oklahoma State University, F–22, pp. 222.1–222.4 (May 1994).
Eck and Garrison, "Management Steps for Predicting Days to Finish (DTF)," Micro Chemical, Inc. (May 1996).
Effertz, "Anxiously Awaiting Alliances," *Beef Today*, pp. 18–20 (Aug. 1994).
Article from *Feed Management*, vol. 36, No. 3, pp. 55–58 (Mar. 1985).
Feuz et al., "Analysis of the Efficiency of Four Marketing Methods for Slaughter Cattle," *Agribusiness*, vol. 9, No. 5, pp. 453–463 (1993) (month not in issue, year sufficiently early).
Fox and Perry, "Predicting Individual Feed Requirement, Incremental Cost of Gain, and Carcass Composition in Live Cattle Varying in Body Size," 8 pp. (Circa more than one year prior to Nov. 12, 1998).
Fox and Tylutki, "Accounting for the Effects of Environment on the Nutrient Requirements of Dairy Cattle," *J Dairy Science*, 81:3085–3095 (1998) (month not in issue, year sufficiently early).
Fox et al., "A Manual for Using the Cornell Net Carbohydrate and Protein System for Evaluating Cattle Diets," Revised for CNCPS Release 2 (Aug. 1993).
Fox et al., "Cornell Cattle Systems 5 Users Guide: Cattle Growth and Profit Prediction Model For All Classes of Growing Cattle," (Circa more than one year prior to Nov. 12, 1998).
Gibb, "Relationships Among Feeder Cattle Characteristics and Subsequent Production Traits," Thesis, Colorado State University (1985) (month not in issue, year sufficiently early).
Gill and Lusby, "Limit Feeding Light–Weight Cattle Height Nutrient Density Diets: Programming Feeding for Calves (PROGFED2,)" *Oklahoma Cooperative Extension Service Current Report*, Oklahoma State University, CR–3025, pp. 3025.1–3025.8 (Jul. 1992).
Gill et al., "Program to Estimate Feedlot Cost of Gain (FLCALC Revision 2)," *Oklahoma Cooperative Extension Service Current Report*, Oklahoma State University, CR–304, pp. 304.1–304.4 (1994) (month not in issue, year sufficiently early).
Gill et al., "Spreadsheet Programs for Calculation of Complete Diets for Beef Cattle, Checking for Nutrient Balance and Estimating Gain," *Oklahoma Cooperative Extension Service Current Report*, Oklahoma State University, CR–3027, pp. 3027.1–3027.8 (Apr. 1994).
Grafel, "Electronic tracking expands role," *Drovers Journal*, p. 12 (Circa more than one year prior to Nov. 12, 1998).
Grafel, "Gettting paid what cattle are worth," *Drovers Journal*, pp. 24, 26 (1994) (month not in issue, year sufficiently early).

Grandin, "Handling Methods and Facilities to Reduce Stress on Cattle," *Veterinary Clinics of North America: Food Animal Practice*, vol. 14, No. 2, pp. 325–341 (Jul. 1998).

Grandin, "The design and construction of facilities for handling cattle," *Livestock Production Science*, vol. 49, pp. 103–120 (1997) (month not in issue, year sufficiently early).

Greathead et al., "The relationship between ultrasonic point readings in live cattle and carcass fat cover," *J. Agric. Sci.*, pp. 651–657 (1984) (month not in issue, year sufficiently early).

Hankins and Berk, "Relationships Among Production and Grade Factors of Beef," [Technical Bulletin No. 665] US Department of Agriculture (Nov. 1938).

Harrison, "Optimizing Marketing Dates for Steers by Accounting for Individual Differences," *Agriculture Economic Report*, No. 372, U.S. Department of Agriculture (Jun. 1977).

Hyer et al., "The Relationship of Body Composition and Feed Intake of Beef Steers," *Animal Science Research Report*, Agriculture Experiment Station, Division of Agriculture, Oklahoma State University (May 1986).

Epley et al., "Prediction of Weight and Percent Retail Cuts of Beef Using Five Carcass Measurements," *J. Animal Science*, 30:872–879 (1970) (month not in issue, year sufficiently early).

Zinn et al., "Feedlot and Carcass Characteristics of Steers and Heifers as Influenced By Days on Feed," *J. Animal Science*, 31:302–306 (1970) (month not in issue, year sufficiently early).

Brown and Shrode, "Body Measurements of Beef Calves and Traits of Their Dams to Predict Calf Performance and Body Composition as Indicated By Fat Thickness and Condition Score," *J. Animal Science*, 33:7–12 (1971) (month not in issue, year sufficiently early).

Brown et al., "Evaluating Relationships Among Immature Measures of Size Shape and Performance of Beef Bulls, II. The Relationships Between Immature Measures of Size, Shape and Feedlot Traits in Young Beef Bulls," *J. Animal Science*, 36:1021–1031 (1973) (month not in issue, year sufficiently early).

Crouse et al., "Prediction of Feeder Calf Performance and Subsequent Carcass Characteristics," *J. Animal Science*, 38:256–263 (1974) (month not in issue, year sufficiently early).

Koch et al., "Characterization of Biological Types of Cattle III. Carcass Composition, Quality and Palatability," *J. Animal Science*, 43:48–62 (1976) (month not in issue, year sufficiently early).

Prior et al., "Influence of Dietary Energy and Protein on Growth and Carcass Composition in Different Biological Types of Cattle," *J. Animal Science*, 45:132–146 (1977) (month not in issue, year sufficiently early).

Koch, "Selection in Beef Cattle III. Correlated Response of Carcass Traits to Selection for Weaning Weight, Yearling Weight and Muscling Score in Cattle," *J. Animal Science*, 47:142–150 (1978) (month not in issue, year sufficiently early).

Koch et al., "Characterizaiton of Biological Types of Cattle–Cycle II: III. Carcass Composition, Quality and Palatability," *J. Animal Science*, 49:448–460 (1979) (month not in issue, year sufficiently early).

Tatum et al., "Carcass Characteristics, Time on Feed and Cooked Beef Palatibility Attributes," *J. Animal Science*, 50:833–840 (1980) (month not in issue, year sufficiently early).

Abraham et al., "Factors Affecting Beef Carcass Cutability: An Evaluation of the USDA Yield Grades for Beef," *J. Animal Science*, 50:841–851 (1980) (month not in issue, year sufficiently early).

Butts et al., "Relationships Among Definable Characteristics of Feeder Calves, Subsequent Performance and Carcass Traits. I. Objective Measurements," *J. Animal Science*, 51:1297–1305 (1980) (month not in issue, year sufficiently early).

Butts et al., "Relationships Among Definable Characteristics of Feeder Calves, Subsequent Performance and Carcass Traits. II. Subjective Scores," *J. Animal Science*, 51:1306–1313 (1980) (month not in issue, year sufficiently early).

Lee et al., "Effect of Cattle Type and Energy Intake on Carcass Traits and Adipose Tissue Cellularity," *J. Animal Science*, 57:621–627 (1983) (month not in issue, year sufficiently early).

Fox and Black, "A System for Predicting Body Composition and Performance of Growing Cattle," *J. Animal Science*, 58:725–739 (1984) (month not in issue, year sufficiently early).

Old and Garrett, "Effect of Energy Intake on Energetic Efficiency and Body Composition of Beef Steers Differing in Size at Maturity," *J. Animal Science*, 65:1371–1380 (1987) (month not in issue, year sufficiently early).

Williams et al., "Comparison of Ultrasound Measurements for Predicting Retail Product and Trimmable Fat in Beef Carcasses," Abstracts form *J. Animal Science*, vol. 66, abstract 213 (1988) (month not in issue, year sufficiently early).

Oltjen and Garrett, "Effects of Body Weight, Frame Size and Rate of an Gain on the Composition of Gain of Beef Steers," *J. Animal Science*, 66:1732–1738 (1988) (month not in issue, year sufficiently early).

Tatum et al., "Influence of Diet of Growth Rate and Carcass Composition of Steers Differing in Frame Size and Muscle Thickness," *J. Animal Science*, 66:1942–1954 (1988) (month not in issue, year sufficiently early).

Williams et al., "The Effects of Muscle Thickness and Time on Feed on Hot Fat Trim Yields, Carcass Characteristics and Boneless Subprimal Yields," *J. Animal Science*, 67:2669–2676 (1989) (month not in issue, year sufficiently early).

Edwards et al., "Using Ultrasound, Linear Measurements and Live Fat Thickness Estimates to Determine the Carcass Composition of Market Lambs," *J. Animal Science*, 67:3322–3330 (1989) (month not in issue, year sufficiently early).

Hicks et al., "Daily Dry Matter Intake by Feedlot Cattle: Influence of Breed and Gender," *J. Animal Science*, 68:245–253 (1990) (month not in issue, year sufficiently early).

Hicks et al., "Dry Matter Intake by Feedlot Beef Steers: Influence of Initial Weight, Time on Feed and Season of Year Received in Yard," *J. Animal Science*, 68:254–265 (1990) (month not in issue, year sufficiently early).

Faulkner et al., "Prediction of Fat Cover and Carcass Composition from Live and Carcass Measurements," *J. Animal Science*, 68:604–610 (1990) (month not in issue, year sufficiently early).

Brackebusch et al., "Relationship Between Longissimus Composition and the Composition of Other Major Muscles of the Beef Carcass," *J. Animal Science*, 69:631–640 (1991) (month not in issue, year sufficiently early).

Phillips et al., "Effect of Pre–and Postweaning Management System on the Performance on Brahman Crossbed Feeder Calves," *J. Animal Science*, 69:3102–3111 (1991) (month not in issue, year sufficiently early).

Bishop et al., "Divergent Selection for Postweaning Feed Conversion in Angus Beef Cattle: I. Mean Comparisons," *J. Animal Science*, 69:4348–4359 (1991) (month not in issue, year sufficiently early).

Kent et al., "Estimates of Beef Carcass Intermuscular Fat," *J. Animal Science*, 69:4836–4844 (1991) (month not in issue, year sufficiently early).

Beltran et al., "Growth Patterns of Two Lines of Angus Cattle Selected Using Predicted Growth Parameters," *J. Animal Science*, 70:734–741 (1992) (month not in issue, year sufficiently early).

Houghton et al., "Application of Ultrasound for Feeding and Finishing Animals: A Review," *J. Animal Science*, 70:930–941 (1992) (month not in issue, year sufficiently early).

Whittaker et al., "Principles of Ultrasound and Measurement of Intramuscular Fat," *J. Animal Science*, 70:942–952 (1992) (month not in issue, year sufficiently early).

Perkins et al., "Evaluation of Ultrasound Estimates of Carcass Fat Thickness and Longissimus Muscle Area in Beef Cattle," *J. Animal Science*, 70:1002–1010 (1992) (month not in issue, year sufficiently early).

Waldner et al., "Validation of Real–Time Ultrasound Technology for Predicting Fat Thickness, Longissimus Muscle Areas, and Composition of Brangus Bulls from 4 Months to 2 Years of Age," *J. Animal Science*, 70:3044–3054 (1992) (month not in issue, year sufficiently early).

Fox et al., "A Net Carbohydrate and Protein System for Evaluating Cattle Diets: III. Cattle Requirements and Diet Adequacy," *J. Animal Science*, 70:3578–3596 (1992) (month not in issue, year sufficiently early).

Coleman et al., "Body and Carcass Composition of Angus and Charolais Stress as Affected by Age and Nutrition," *J. Animal Science*, 71:86–95 (1993) (month not in issue, year sufficiently early).

Park et al., "Divergent Selection for Postweaning Feed Conversion in Angus Beef Cattle: III. Linear Body Measurements of Progeny," *J. Animal Science*, 71:334–340 (1993) (month not in issue, year sufficiently early).

Owens et al., "Factors that Alter the Growth and Development of Ruminants," *J. Animal Science*, 71:3138–3150 (1993) (month not in issue, year sufficiently early).

Nour and Thonney, "Technical Note: Chemical Composition of Angus and Holstein Carcasses Predicted from Rib Section Composition," *J. Animal Science*, 72:1239–1241 (1994) (month not in issue, year sufficiently early).

Swatland et al., "A Review of Probes and Robots: Implementing New Technologies in Meat Evaluation," *J. Animal Science*, 72:1475–1486 (1994) (month not in issue, year sufficiently early).

Herring et al., "Evaluation of Machine, Technician, and Interpreter Effects on Ultrasonic Measures of Backfat and Longissimus Muscle Area in Beef Cattle," *J. Animal Science*, 71:2216–2226 (1994) (month not in issue, year sufficiently early).

Gwartney et al., "The Effects of Orientation and Storage Time on the Prediction of Beef Rib Composition Using Electromagnetic Scanning," *J. Animal Science*, 73:387–392 (1995) (month not in issue, year sufficiently early).

Shackelford et al., "Predicting Beef Carcass Cutability," *J. Animal Science*, 73:406–413 (1995) (month not in issue, year sufficiently early).

Perry and Fox, "Predicting Carcass Composition and Individual Feed Requirement in Live Cattle Widely Varying in Body Size," *J. Animal Science*, 75:300–307 (1997) (month not in issue, year sufficiently early).

Jeffrey et al., "Weight–based Adjustment for Ultrasonically Derived Carcass Traits Among Performance Tested Angus Bulls," *Animal Science Research Report*, pp. 49–54 (1993) (month not in issue, year sufficiently early).

Brethour, "Using Ultrasound Technology to Increase Cattle Feeding Profits," *KAES Report of Progress No. 570*, Fort Hays Branch Experiment Station, Kansas State University, pp. 5–12 (Apr. 1989).

Olson, "Efffect of Winter Environment (Range vs Drylot) on Replacement Heifer Development and Behavior," *KAES Report of Progress No. 597*, Fort Hays Branch Experiment Station, Kansas State University, pp. 1–33 (Apr. 1990).

Brethour, "Relationships of Ultrasound–Measured Backfat to Feedlot Performance of Beef Steers," *KAES Report of Progress No. 627*, Fort Hays Branch Experiment Station, Kansas State University, pp. 1–30 (Apr. 1991).

Brethour, "Quality Management in the Cattle Industry," *KAES Report of Progress No. 653*, Fort Hays Branch Experiment Station, Kansas State University, pp. 1–25 (Apr. 1992).

Brethour, "Technology to Implement Quality into Beef Production," *KAES Report of Progress No. 706*, Fort Hays Branch Experiment Station, Kansas State University, pp. 13–17 (Circa more than one year prior to Nov. 12, 1998).

Bolsen and Young, "Agronomic Performance and Silage Quality Traits of Sorghum Hybrids in 1992 and 1994," *KAES Report of Progress No. 731*, Fort Hays Branch Experiment Station, Kansas State University, pp. 1–26 (Apr. 1995).

Brethour, "Evaluating Calves with Ultrasound at Weaning for Future Carcass Potential," *KAES Report of Progress No. 808*, Fort Hays Branch Experiment Station, Kansas State University, pp. 1–4 (Apr. 1998).

Lusby and Gill, "Basic Considerations for Rations and Supplements," *OSU Extension Facts*, Oklahoma Extension Service, Oklahoma State University, No. 3012, pp. 3012.1–3012.2 (Mar. 1982).

Lusby and Gill, "Formulating Complete Rations," *OSU Extension Facts*, Oklahoma Extension Service, Oklahoma State University, No. 3013, pp. 3013.1–3013.4 (Mar. 1982).

Lusby and Gill, "Spreadsheet for Calculating Livestock Rations," *OSU Extension Facts*, Oklahoma Extension Service, Oklahoma State University, No. 3024, pp. 3024.1–3024.4 (Jul. 1991).

Lusby and Gill, "Stocker Cattle Nutrition III: Formulating Supplements," *OSU Extension Facts*, Oklahoma Extension Service, Oklahoma State University, No. 3014, pp. 3014.1–3014.4 (Jul. 1982).

Maday, "Cattle Sorting Enters a New Age," *DJ Feeder Management*, pp. 1–5 & 8 (Sep. 1994).

McPeake, "Hip Height and Frame Score Determination," *OSU Extension Facts*, Oklahoma Extension Service, Oklahoma State University, F 3271, pp. 3271.1–3271.2 (Circa more than one year prior to Nov. 12, 1998).

Miller et al., "Evaluation of Live and Carcass Techniques for Predicting Beef Carcass Composition," *Meat Science*, pp. 111–129 (1988) (month not in issue, year sufficiently early).

Murray et al., "Effects of three different growth rates on empty body weight, carcass weight and dissected carcass composition of cattle," *J. Agric Sci.*, vol. 82, pp. 535–547 (1974) (month not in issue, year sufficiently early).

Oringderff, "A Little Black Box," pp. 39–44 (Circa more than one year prior to Nov. 12, 1998).

Sainz and Oltjen, "Improving Uniformity of Feeder Steers Using Ultrasound and Computer Modeling," *Proceedings, Western Section, American Society of Animal Science*, vol. 45, pp. 179–181 (1994) (month not in issue, year sufficiently early).

Tatum, "Effects of Management History, Breed–Type and Carcass Characteristics on Palatability Attributes of Beef," Dissertation, Texas A&M University (Aug. 1978).

Tatum, "Evaluation of Ultrasound and Visual Appraisal for Estimation of Fat Thickness and Ribeye Area in Live Cattle," pp. 99–103 (Circa more than one year prior to Nov. 12, 1998).

Thornton et al., "Feed Intake by Feedlot Beef Steers: Influence of Initial Weight and Time on Feed," *Animal Science Research Report*, Agriculture Experiment Station, Division of Agriculture, Oklahoma State University, pp. 321–331 (1985) (month not in issue, year sufficiently early).

Williams et al., "Simulated influence of postweaning production system on performance of different biological types of cattle. II. Carcass composition, retail product and quality," Roman L. Hruska US Meat Animal Research Center, Clay Center, Nebraska, pp. 1–28 (Circa more than one year prior to Nov. 12, 1998).

* cited by examiner

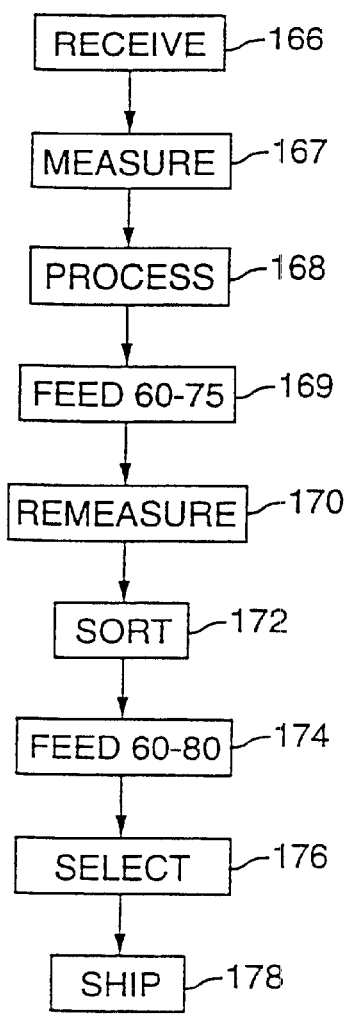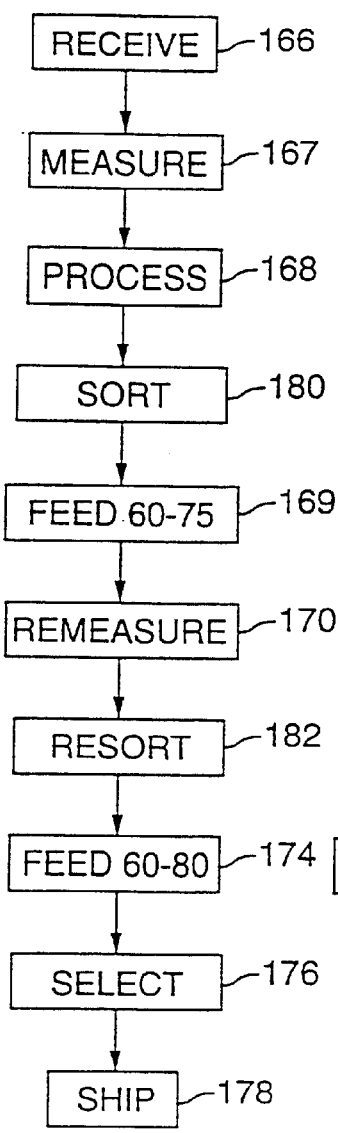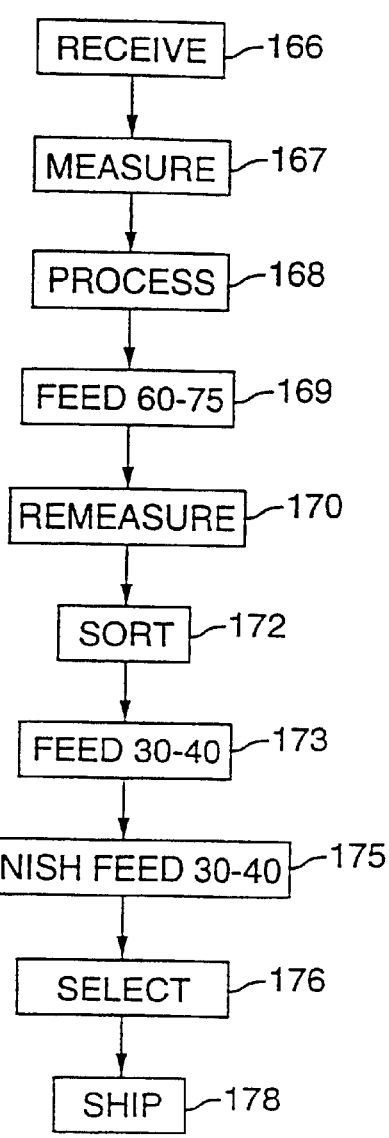

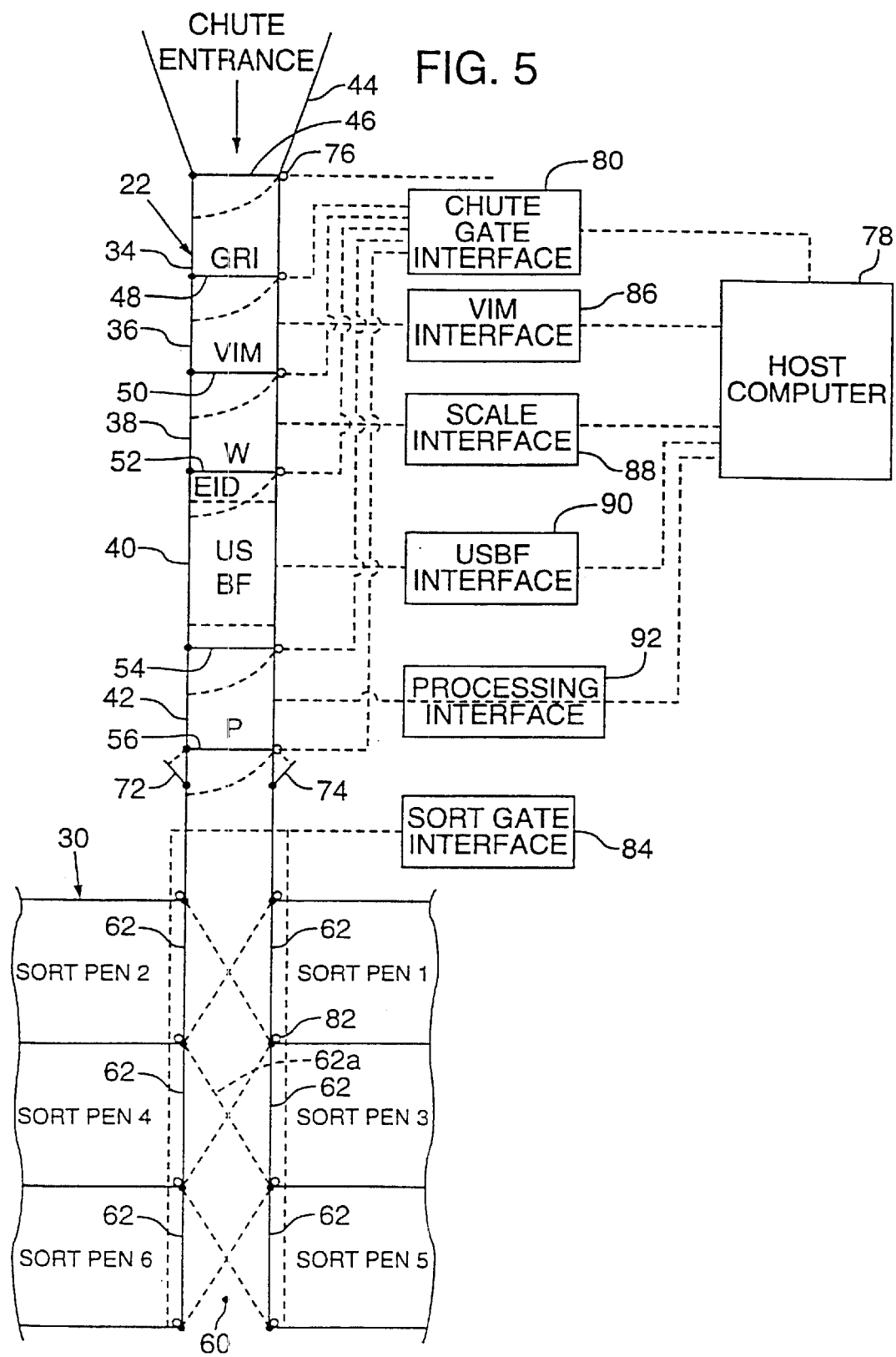

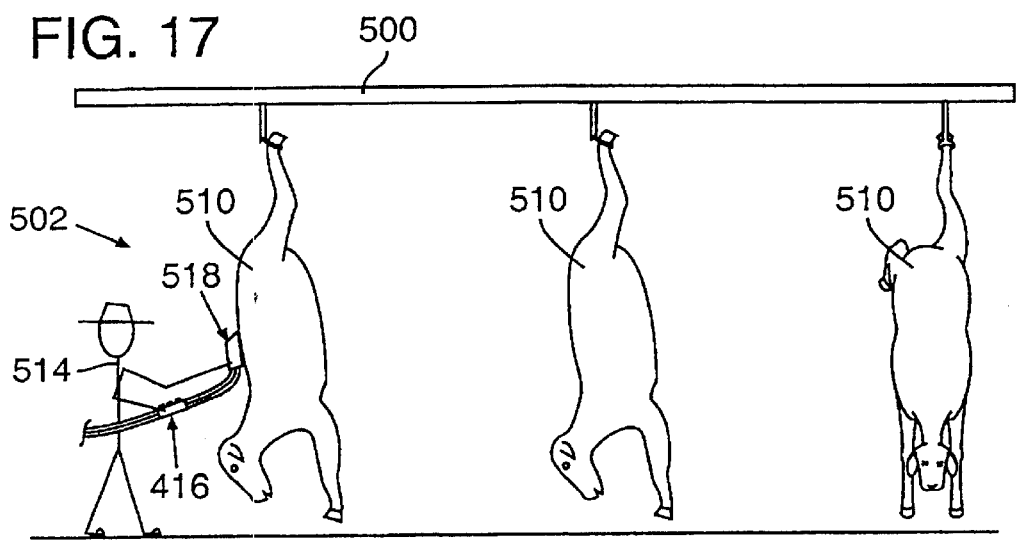
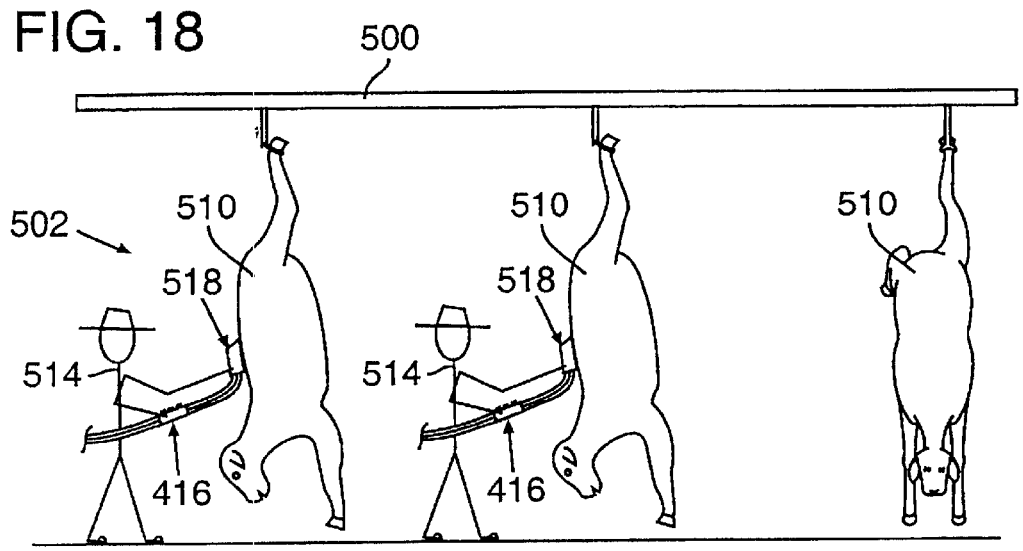

RUMINANT TISSUE ANALYSIS AT PACKING PLANTS FOR ELECTRONIC CATTLE MANAGEMENT AND GRADING MEAT

CROSS REFERENCE TO RELATED APPLICATIONS

The present application is a continuation of U.S. patent application Ser. No. 09/190,916, filed on Nov. 12, 1998, now issued as U.S. Pat. No. 6,200,210, which was a continuation-in-part of U.S. patent application Ser. No. 08/838,768, filed on Apr. 10, 1997, now issued as U.S. Pat. No. 6,000,361, and U.S. patent application Ser. No. 08/748,220, filed on Nov. 12, 1996, now issued as U.S. Pat. No. 5,836,880. These prior applications are incorporated herein by reference.

FIELD OF THE INVENTION

The present invention concerns performing ultrasound tissue imaging and analysis to measure internal tissue characteristics of ruminants at packing plants during processing but prior to reaching the carcass stage, and using data obtained by such analysis for improved management of feedlot and packing plant processing of ruminants and objectively determining meat quality and yield.

BACKGROUND

The cattle growth, production and processing industry comprises four major components, producers, feedlots, packing plants and wholesalers/retailers. The cattle producers maintain cowherds. The herds produce calves that are raised and grown on pasture grazing land, much of which is unsuitable for cultivation. The calves are grown to a certain size, after which they are moved to a confined feedlot. Cattle are then processed for consumers at packing plants.

A. Feedlots

Feedlots generally care for thousands of head of cattle or other ruminants (ruminants are cud chewing, quadruped hoofed mammals of the suborder Ruminantia, and include domestic cattle, sheep, goats, bison, buffalo, deer, and antelopes) at once in various stages of growth. These animals come from a variety of sources with widely varying previous care and feeding performance history. Cattle within a feedlot are physically contained in cattle pens, each pen typically having a feed bunk to receive feed, a water source for drinking and manually-operated gates to enter and exit the pens. A feedlot typically includes: (a) a receiving area where cattle are contained upon their arrival at the feedlot; (b) a processing area where cattle, shortly after their arrival, are tagged, weighed and given health care and growth promotant products; (c) a hospital area where individual animals that are ill or otherwise in need of treatment can be medicated or otherwise treated and returned to their pens; and (d) a shipping area where cattle are prepared for shipment to a packing plant for slaughter.

Although feedlot sizes range from a one-time capacity of a few heads to a capacity of over one-hundred-thousand head, the trend in North America is towards large feedlots in the ten thousand to one-hundred-thousand head capacity. These larger feedlots feed the majority of feedlot-fed cattle in North America intended for beef consumption.

The owners of particular cattle in a feedlot are defined by a unique lot number. The number of cattle in a lot may vary, and an owner may own a portion of a lot, a portion of multiple lots, or all of one or more lots. Each lot may occupy one or multiple pens. Animals also may each be identified by a unique individual number.

Proper care for animals in a large feedlot is a complex and time-consuming task because of, for example, feeding, water supply, insect control, and individual or group treatment requirements. Treatments may include group treatments where various medications are added to the feed, or individual treatments that are applied topically, orally, by injection or by implantation to selected individual or groups of animals.

Regular sorting of animals also occurs. Animals at a feedlot may be moved individually and in groups several times during the several-month period each animal is kept in the feedlot. This movement of animals from their home pen to other pens, from a home pen to a treatment area and later return, and from several pens into a common pen, is necessary for the proper care and maintenance of the animals.

Feedlots assess various charges to owners for the care and maintenance of their animals. These charges typically are assessed by lot number at periodic intervals based on feedlot care and maintenance records, not on an individual animal basis (except for individual hospital treatments). Examples of assessed charges include ration charges in dollars-per-ton, health care and growth promotion product charges, a daily yardage fee per head, and handling charges.

Within the feedlot cattle population, there is tremendous diversity in individual animal characteristics, such as weight, frame size, muscling, fat content and deposition rate, breed type, rate of gain, feed efficiency, intramuscular fat (marbling), sex, age, health and drug treatments, nutrition and growth history, and other factors. The diverse beef cattle population results in an extremely variable beef product for the consumer in terms of eating quality, fatness, tenderness, size of cuts and other factors. It has been a primary goal of the beef industry associations to improve the quality and uniformity of beef for the American consumer for many years. The 1991 Beef Quality Audit identified approximately $280 per head being wasted, of which more than $150.00 was excess fat.

In order to improve the current beef product, it is first necessary that the current diverse cattle population is managed for optimum efficiency and desired carcass cut out quality and value for the consumer. Second, ultimately the genetic make up of the producer cowherd must be changed. The livestock industry has tried for years, with limited success, to improve the genetics of the cattle population to produce the types of animals that will yield a high percentage of lean meat with a low percentage of fat efficiently, and also provide a desirable and also provide a desirable eating quality for the consumer. However, there has been no effective way for large feedlots to: (a) measure and sort animals individually; (b) keep accurate and complete records of live physical characteristics and charges for each animal; or (c) produce an economic end point determination for each animal using growth performance data. There also has there been no effective way to match growth performance data to end-product carcass data for each animal from slaughtering operations that would enable a correlation between carcass value and live animal performance and measured characteristics so as to help identify superior genetic types for future breeding and management purposes, and to identify management practices that will maximize the value of the arrival in the market.

Based on the above, there clearly is a need to be able to measure and track the physical and performance characteristics of each animal during its residence in the feedlot for determining an optimum marketing date. Ideally, the physical and growth characteristics of each animal should be known at every stage of its stay in the feedlot in order to determine when the animal should be slaughtered for optimum growth efficiency and value of the carcass based upon a carcass grading target and market conditions.

There also is a need for a method for obtaining yield and grade information for each animal as soon as it is processed at a packing plant. This information would further help feedlot operators better determine how to manage cattle at feedlots and help producers to improve genetics. Currently, grading information is based generally on government grading, which is done solely by visual inspection with intermittent checks by manual measurements. Actual yield and quality grade information for each animal processed by a packing plant is not available until the government grading has been completed, which typically is two or more days after an animal has been processed by the packing plant. Sometimes rib eye tracings also are used for grading, but these tracings take from several hours to several days to obtain and analyze following the typical two-day grading delay. Real time information from the packing plant prior to processing each animal to a carcass concerning each animal's yield and quality grade has heretofore not been available.

Methods and systems used prior to the present invention have been too inaccurate or lack the capability to identify and track characteristics of performance and charges on an individual animal basis. Additionally, they have been too labor intensive and too injurious to animals, and have required skill levels not readily available in feedlots or packing plants. Some of these prior known methods and systems are discussed below.

Pratt U.S. Pat. Nos. 4,733,971, issued Mar. 29, 1988, 4,889,433, issued Dec. 26, 1989, 4,815,042, issued Mar. 21, 1989, 5,219,224, issued Jun. 15, 1993, and 5,340,211, issued Aug. 23, 1994, address the problem of delivering feed additives into animal feed rations in a feedlot accurately and on a customized basis at the time of feeding. Pratt U.S. Pat. No. 5,008,821, issued Apr. 16, 1991, addresses the problem of determining accurately the amount of feed ration to deliver to a particular pen of animals at each feeding. Pratt U.S. Pat. No. 5,315,505, issued May 24, 1994, addresses the problem of keeping track of drug inventories, drugs administered to particular animals, and animal health histories in a cattle feedlot, and determining what drugs or combinations thereof should be administered, and in what dosages, to a particular animal diagnosed with a specific illness.

While the foregoing patents address important aspects of cattle management in a feedlot, they do not address the broader aspect of how, when and how often to measure, sort, feed and treat animals in a feedlot, how long to feed them, and how and when to select them for shipment from the feedlot.

Hayes U.S. Pat. No. 4,745,472, issued May 17, 1988, and others, have proposed ways to accurately measure an animal's external dimensions by scanning using video imaging techniques. Similarly, ultrasound backfat measurement of cattle is known, at least on an experimental basis, from the work of Professor John Brethour of Kansas State University's Fort Hayes Experimental Station, as explained in an article entitled "Cattle Sorting Enters a New Age" appearing at pages 1–5 and 8 of the September 1994 issue of *D.J. FEEDER MANAGEMENT*. Professor Brethour has, on an experimental basis, used the data from such measurements to project an estimated optimum shipping or end date (OED) for the measured animals.

Various methods for sorting and weighing cattle have been known or proposed, as disclosed, for example, in Linseth U.S. Pat. No. 4,288,856, Hayes U.S. Pat. No. 4,617,876, and Ostermann U.S. Pat. No. 4,280,448. Cattle Scanning Systems of Rapid City, S. Dak., markets a computerized video imaging and sorting system that includes weighing and scanning external dimensions of each animal, assigning a frame score and muscle score to the animal based on such dimensions, calculating a predicted optimal end weight and marketing date from the composite score and current weight data, and then sorting the animals for feeding according to their optimal marketing dates.

Recently, Brethour has suggested using data from ultrasound backfat measurement of individual animals, 60–80 days into a feeding period, and a computer modeling program, to physically sort cattle into groups according to projected marketing dates as they are measured, apparently based on the ultrasound-generated data alone. Pratt U.S. Pat. No. 5,573,002, which is incorporated herein by reference, describes an ultrasound device useful for making internal tissue measurements of feed animals. Pratt '002 patent describes a device and method particularly useful for making tissue measurements on live animals restrained in a stall. Pratt U.S. Pat. No. 5,836,880, also incorporated herein by reference, describes an automated version of an ultrasound tissue analyzer useful for analyzing internal tissue characteristics in animals. Both of Pratt's prior applications are primarily concerned with making tissue analyses on animals at a feedlot.

Hayes U.S. Pat. No. 4,617,876 discloses a computerized system for controlling, by weight, the movement and location of individual animals within one or multiple pens in a feedlot using a system of animal watering and weighing stalls and electronic ear tags to identify each animal. The weight of an animal as measured within the stall determines where the animal is routed within sections of a pen or among multiple pens. Although the Hayes '876 patent suggests generally that criteria other than weight may be used to control the operation of a stall exit gate and other gates to route an animal to a desired location, it does not suggest how such other criteria could be efficiently obtained, or that such criteria could be used to determine an animal's economic and physical performance and value, or to improve future feedlot management practices or future breeding and selection practices. Nor does Hayes '876 suggest that combinations of two or more criteria may be used to route an animal or determine its location within multiple pens or other areas.

The Linseth patent discloses a computerized method of sorting animals in a feedlot according to weight gain. Each incoming animal is identified and weighed in a walk-through scale, and its identification and weight are recorded. At a later date, each animal is reweighed in the walk-through scale and its weight gain is determined. From this determination, the animals are sorted into pens according to weight gain, and underperforming animals are culled from the group.

B. Packing Plant

After their stay at feedlots, ruminants are processed at a packing plant. At the packing plant, the animal is first stunned. The stunned animal is then picked up by an overhead trolley using a leg shackle and bled. The trolley can move as many as 400 hundred cattle per hour to other locations in the packing plant for processing into carcasses. Carcasses are formed by removing the feet, hide, viscera, head and tails. The carcasses are then conveyed to coolers for storage and subsequent grading by inspectors.

As discussed above, cattle currently are graded at the packing plant only after processing into carcasses and chilled, which takes at least forty-eight hours. The grade of the meat produced by particular cattle is judged subjectively by a government grader. The government grader has only a few seconds to visually inspect the carcass and assign a grade. This inspection may be done as the carcass is conveyed past the inspector. The grading also may be supplemented using other measurements, such as a rib eye muscle trace. This involves actually tracing the rib eye muscle with tracing paper. This tracing is then taken elsewhere to either manually calculate the rib eye area, or to use a machine to view the tracing paper and provide a determination as to the rib eye muscle area.

There are a number of problems associated with the current grading system, including: (a) differences in grading between graders; (b) animals that are either substantially better than average or substantially worse than average tend to be graded closer to average by visual inspection methods by all inspectors than is justified; (c) the process of removing the animal's hide during processing to form a carcass also removes some of the backfat, which commonly distorts backfat measurements and thus the true yield grading of the meat produced from a ruminant animal. Furthermore, the quality and yield grade results obtained at the packing plant for each animal determines the price paid for a particular animal for those receiving income for raising the animal, processing the animal at the feed lot and for processing the animal at the packing plant. Using conventional systems known prior to the present invention, data for a processed animal is not available until after the carcass has been formed and graded by the government grader. This delays determining the price-per-animal and paying those in the processing line, such as the ranchers and feedlot operators, for the value of the animal. Currently, packing plant operators do not pay feedlot operators on the basis of individual animal measurements made at the feedlot, but instead make payments based on individual carcass grades at the packing plant. As a result, payment to the feedlot is delayed for at least two days.

Packing plant operators also do not have a good inventory classification until the grading information is provided. This makes it difficult to plan inventory distribution and future buying decisions.

None of the known methods or systems use more than two criteria for selecting, sorting or predicting an optimal marketing date. Also, none teaches or suggests a way in which such prior methods or systems might be integrated into a total system of cattle management for maximum economic return to the feedlot and the producer, and for optimum use of the accumulated data for each animal to determine production costs of each animal and to improve the genetics of future breeding stocks.

Thus, while many methods for measuring and selecting cattle in feedlots have been tried, both visual and automated, none have been successful in accomplishing the desired end-result. That end-result is the ability to select a given animal for shipment from the feedlot to the packing plant at the optimum time, considering the animal's condition, performance and market factors, the ability to grow the animal to its optimum individual potential of physical and economic performance, and the ability to record and preserve each animal's performance history in the feedlot and carcass data from the packing plant for use in cultivating and managing current and future animals for meat production. The beef industry is extremely concerned with its decreasing market share relative to pork and poultry. Yet to date, it has been unable to devise a system or method to accomplish on a large scale what is needed to manage the current diversity of cattle to improve the beef product quality and uniformity fast enough to remain competitive in the race for the consumer dollar spent on meat.

SUMMARY

The present invention addresses the problems noted above with grading and tissue analysis devices known prior to the present invention. The method of the present invention allows meat packers to know what is in inventory much sooner than is possible using conventional methods, such as the subjective grading approach used by government graders. For example, using the method of the present invention, packing plants now can determine inventory much sooner than before, such as at least about 48 hours sooner. Moreover, the data obtained at this earlier stage using ultrasound devices is less subjective, and tends to correlate better, with the actual meat yield of the animal subsequent to processing.

A method for eliminating the subjectivity of meat grading and providing such data much earlier in the process has been needed for some time. Inventions prior to the present invention generally have failed. One reason for this is that measuring tissue characteristics in a packing plant is difficult because of the time constraints imposed on personnel by the meat packing process. After an animal is stunned, it is then suspended on a conveying system for conveying the animal to other locations for further processing. Packing plants may process more than 400 hundred head of cattle an hour. Any tissue analysis done at the packing plant therefore must account for the fact that the cattle are being conveyed rather quickly from location-to-location. This provides personnel attempting to make measurements on the stunned animal difficulties, as approximately only about 10 seconds, and more typically about 5–7 seconds are provided for such personnel to make the required tissue measurements. And, the animal is moving at the time the ultrasound measurements are made. This makes it more difficult for the personnel conducting the tissue analysis to apply ultrasound-enhancing fluid to the animal and properly position the ultrasound device for the analysis.

These problems have been solved by the method of the present invention. One embodiment of the method comprises stunning a ruminant at a packing plant, and thereafter measuring tissue characteristics of the ruminant using a tissue imaging and analysis device prior to processing the ruminant to a carcass. The ruminants typically are conveyed seriatim to a position adjacent the device. The device is then used to analyze tissue characteristics of a different ruminant every 30 seconds or less, and generally every 15 seconds or less. Working embodiments of the method have used an ultrasound tissue imaging and analysis device, although other analyses also can be performed. Working embodiments of the ultrasound tissue imaging and analysis device comprised a liquid reservoir containing a conductive liquid, an ultrasonic transducer, a hand-held handpiece for positioning the ultrasonic transducer adjacent livestock, the handpiece further comprising a dispenser for dispensing liquid from the reservoir onto the livestock, a liquid conveying mechanism, such as a pump, liquidly connected to both the reservoir and the dispenser, and a computer electrically coupled to the transducer. To perform tissue analysis, the transducer is positioned between rib 12 and 13.

The ultrasound analysis can be performed by one operator, or plural operators. For example, if the device is an ultrasound tissue analysis device, the step of conveying may first comprise conveying the ruminant to a position adjacent a first operator. The first operator applies an ultrasound image enhancing fluid to the ruminant's hide. The ruminant is then conveyed to a position adjacent a second operator. The second operator places the ultrasound tissue analysis device adjacent the enhancing fluid and performs ultrasound tissue imaging and analysis on the ruminant. The method can be used to, amongst other things, measure backfat and rib eye dimensions, obtain an ultrasound image, and determine rib eye area and marbling using the measured tissue characteristics. This data can then be used to perform grading calculations, such as to determine quality and/or yield grades.

The present invention also provides a method for monitoring the raising and processing of ruminants in a feedlot and packing plant. The method comprises first measuring internal tissue characteristics and/or external body dimensions (also referred to herein as body measurements) of ruminants at a feedlot. Information obtained concerning each ruminant is stored in a computer or on computer-readable medium. These ruminants are then fed and maintained at the feedlot. The ruminants are then shipped to a packing plant. At the packing plant, tissue characteristics of stunned ruminants are measured using a tissue imaging and analysis device prior to processing the ruminants to carcasses. Measurements made for each animal at the feedlot are correlated with measurements made at the packing plant. Moreover, yield and quality values are determined in real time for each ruminant based on measurements made at the feedlot and packing plant.

BRIEF DESCRIPTION OF THE DRAWINGS

FIGS. 4A, 4B, and 4C are cattle processing diagrams illustrating three alternative methods of processing and managing cattle in a feedlot in accordance with the method of the present invention.

FIG. 5 is an enlarged schematic diagram of the single-file measuring chute and adjacent sorting pens similar to those shown in FIG. 1, but on an enlarged scale and showing schematically a control means for controlling the operation thereof.

FIG. 17 is a schematic drawing illustrating an operator using an ultrasound tissue analyzer in a packing plant for analyzing backfat on a stunned ruminant conveyed to the operator after being stunned and bled.

FIG. 18 is a schematic drawing illustrating an alternative method for measuring internal tissue characteristics of a stunned ruminant using a first operator to apply a conductive liquid to a stunned ruminant conveyed to the first operator after being stunned and bled, and a second operator to take ultrasound measurements on the ruminant following the application of conductive liquid.

DETAILED DESCRIPTION

The present invention provides a method for analyzing tissue characteristics of ruminants, particularly cattle, at a packing plant. The information provided by the tissue analysis is then used to, amongst other things: (a) determine the price paid for each ruminant; (b) determine the yield and quality of the meat processed from each ruminant; (c) make management decisions concerning how to better process cattle at feedlots; and (d) better track and manage inventory and product distribution by packing plants. As used herein, "yield" refers to yield grade (which is a grading scale from 1–5, with 1 being the best and 5 the worst), and/or red meat yield percent (which typically ranges from about 45% to about 55%). The following paragraphs describe working embodiments of electronic cattle management at feedlots, an ultrasound tissue analysis device for conducting tissue analysis at packing plants, a method for using the data obtained at the packing plant for making management decisions at the feedlot, a method for determining yield and quality values for ruminants in real time while processing the cattle at the packing plant, and a method for making inventory management decisions by packing plant operators.

I. Electronic Cattle Management
A. Description of Feedlot

Figure 1:
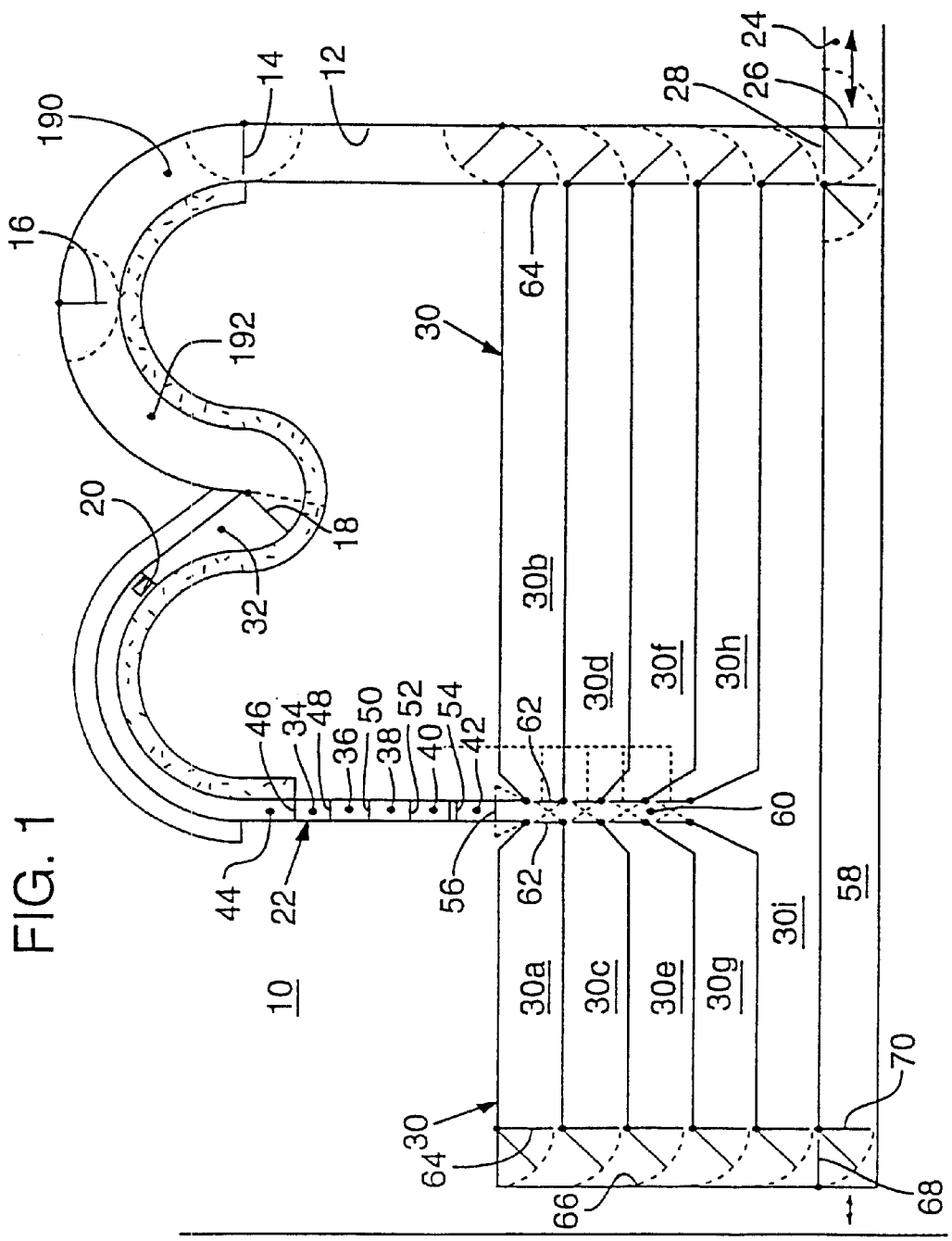
FIG. 1 is a schematic diagram of the layout of the single-file cattle processing chute and sorting pen portion of a feedlot in accordance with the invention.

FIG. 1 illustrates a feedlot 10 which would typically include a series of feed pens (not shown) where cattle would be fed selected feed rations and watered during their stay in the feedlot. For example, four feed pens A, B, C and D are illustrated schematically in FIG. 7. In addition to feed pens, a feedlot incorporating the cattle management system and method of the invention includes an alley 12 leading through a series of manually or power-operated gates 14, 16, 18 and a one-way gate 20 to a chute 22.

Alley 12 leads from an alley 24 which communicates with both feed pens and receiving and holding pens, where cattle are received and held for a short period upon their delivery to the feedlot from a producer. The intersection of alley 24 and the alley 12 leading to the chute 22 is gated as indicated at 26 and 28 to control the admission of cattle into alley 12 leading to the chute and to control the exit of cattle from sorting pens indicated at 30.

The gates 14, 16 and 18 subdivide the upper curved portion of alley 12 into cattle holding sections 190, 192 of about 40 head apiece so as to control the delivery of cattle into a crowding section 32 through crowd gate 18. Crowding section 32 narrows from its entrance to the one-way gate 20 so that cattle are forced single file through the gate 20 and into the chute area 22 which is a single-file chute.

Chute section 22 is subdivided into a series of longitudinally arranged stations 34, 36, 38, 40 and 42. These five stations are separated from one another and from the entrance 44 to the chute by entrance and exit gates 46, 48, 50, 52, 54, 56. The stations defined by these gates are only large enough to receive one animal at a time. The opening and closing of these gates are controlled by position sensors such as photoelectric cells under computer control to control the one at a time movement of animals through the chute. A larger scale depiction of the chute will be seen in FIG. 5.

Just downstream of the single-file chute are a series of the previously mentioned sorting pens 30, there being nine such pens illustrated in FIG. 1, including pens 30A, 30B, 30C, 30D, 30E, 30F, 30G, 30H and 30I. Below these pens in FIG. 1 is an alley 58 leading from the left-hand pen exits to the alleys 12 and 24. In addition, there is a single-file narrow alley 60 between the left-hand series of sorting pens 30A, 30C, 30D, 30E, 30G and the right-hand series of sorting pens 30B, 30D, 30F and 30H. From the layout of FIG. 1 it will be apparent that any animal proceeding through the chute and not sorted into one of the sorting gates 30A–30H will automatically end up in sorting pen 30I.

Alley 60 is normally isolated from the entrances to each of the eight sorting pens 30A–30H by a computer-operated entrance gate 62 at the entrance to each sorting pen. There is no entrance gate to the final sorting pen 30I. Each sorting pen also has an exit gate 64 at its opposite end opening into an alley used to direct the cattle from the sorting pens to another destination to be described in greater detail below. The exit gates 64 on pens 30A, 30C, 30E and 30G on the left-hand side of the alley 60 in FIG. 1 open into an alley 66 leading through control gates 68, 70 back to alley 58 where cattle can be directed either back through alley 12 or into alley 24 leading to the feed pens.

Each station of the single file chute 22 is set up either to prepare each animal for measurement or processing, or to actually measure or process the animal. For example, in FIG. 1, station 34 is termed the "get ready" station where one animal is admitted from the chute entrance area 44. Once the animal enters the "get ready" station 34, gate 46 closes and gate 48 remains closed so the animal remains isolated at that station. Then gate 48 is opened so that the animal enters the next station 36. Station 36 is where certain external dimensions of each animal are measured. This is preferably done through a video-imaging device or scanner suitable for this purpose such as one known commercially as an MSI Scanner available from Cattle Scanning Systems (C.S.S.) of Rapid City, S. Dak. Another video-imaging measurement system for cattle is disclosed in Hayes, U.S. Pat. No. 4,745,472.

After the animal's external dimensions are measured, gate 50 is opened and the animal proceeds into the third station 38 in the chute which contains a scale on which the animal is weighed. The scale used can be any of a number of commercially available scales but should be capable of generating an electronic signal for recording the weight at a remote location. Also at the scale station or at another desired station, an electronic identification (EID) tag is attached to the animal's ear. This EID tag remains attached to the animal throughout its residence in the feedlot and its shipment to the packing plant where it is removed upon slaughter. Through this EID tag, the animal can not only be identified but its location can be tracked and its measurement and performance data correlated to the animal throughout the duration of its feedlot stay, through its shipment to the packing plant, and until slaughter. One suitable EID tag for this purpose is manufactured by Allflex International and is described in greater detail in U.S. Pat. No. 5,315,505, issued May 24, 1994, to the assignee of the present application. The disclosure of U.S. Pat. No. 5,315,505 is incorporated herein by reference. The Allflex EID tag is a transponder which operates through a nearby antenna and an integrator reader also available from Allflex International. Each EID tag emits a signal unique to the animal to which it is attached, which is electronically "read" by the antenna and communicated to a host computer via a computer interface unit.

After an animal's weight is recorded and its EID tag attached, it moves through gate 52 to the next measuring station 40 where its internal backfat content is measured using an ultrasound measuring means and technique. For this purpose, the animal must be held fairly still, station 40 is a "squeeze chute", well known in the feedlot industry. The squeeze chute has a rear gate that pushes against the rear of an animal while its head is stabilized in a "head catcher". One embodiment of an ultrasound backfat measuring system used at station 40 is described in more detail below. An alternative embodiment of an ultrasound backfat measuring system has been adapted from the experimental system used by Professor John Brethour at Kansas State University's Fort Hays Experiment Station, described in the September 1994 issue of *DJ Feeder Management magazine*.

After backfat measurement, the gate 54 is opened and the animal proceeds to station 42 for processing. Station 42 is also a squeeze chute. Typically, processing at station 42 will include individual drug administration, growth hormone implantation, castration and dehorning. After processing, the cute exit gate 56 is opened and the animal is sorted into one of the sorting pens.

The enlarged schematic version of the single-file chute 22 shown in FIG. 5 is sufficiently similar to the cute 22 shown schematically in FIG. 1 that the same reference numerals will be used in describing both chutes. With reference to FIG. 5, it includes the same five processing and measuring stations 34, 36, 38, 40 and 42 as in FIG. 1. However, at the downstream end of the chute 22 of FIG. 5, there are only six sorting pens 30 shown and designated sort pens 1–6, rather than nine such pens as shown in FIG. 1.

As shown most clearly in FIG. 5, the single-file chute includes at its downstream end just downstream of chute exit gate 56 from the processing station 42 a pair of access gates 72, 74 for the admission of feedlot personnel into the chute when necessary. These gates may be manually operated. From FIG. 5 it will also be apparent that sorting into one of the several sorting pens is accomplished after each animal proceeds through all five stations of the chute by opening an entrance gate to one of the sorting pens while the others remain closed. Thus, for example, if an animal is to be sorted into sorting pen 3 in FIG. 5 its entrance gate 62 would open to the position 62a shown while the entrance gate 62 to all other sorting pens remain closed, thereby directing the animal into sorting pen 3.

As previously mentioned, each sorting pen entrance gate 62 and each of the chute gates 46, 48, 50, 52, 54 and 56 is operated via position sensors indicated schematically at 76 in FIG. 5 in conjunction with a host computer 78 through chute gate interfaces indicated schematically at 80.

Similarly, sort pen entrance gates 62 are operated by the position sensors 82 controlled by the host computer 78 through the sort gate interfaces 84.

The measurement taken at each of the measuring stations 36, 38 and 40 of the chute, for each animal passing through the chute, transmits a signal indicative of the measurement for that animal through an appropriate interface to the host computer 78, where the measurement data is entered and stored for use in calculating various performance characteristics of the animal.

Each measurement is correlated with a specific animal through the animal's EID tag as it passes from station to station through the chute. More specifically, the video imaging measurement (VIM) data is transmitted through a VIM interface 86 to the host computer 78. Weight data for the same animal is transmitted from the scale at station 38 through a scale interface 88 to the host computer 78. Then the ultrasound backfat data for the same animal is transmitted through the USBF interface 90 to the host computer 78. Finally, any drugs administered to the animal or other procedures performed on the animal at the processing station 42 are transmitted through the processing interface 92 to the host computer where such data is correlated with the animal processed.

Reference is made to the aforementioned U.S. Pat. No. 5,315,505 for a detailed description of how animal health data and drug administration data would be entered into the host computer from a processing station for a given animal.

Figure 2:
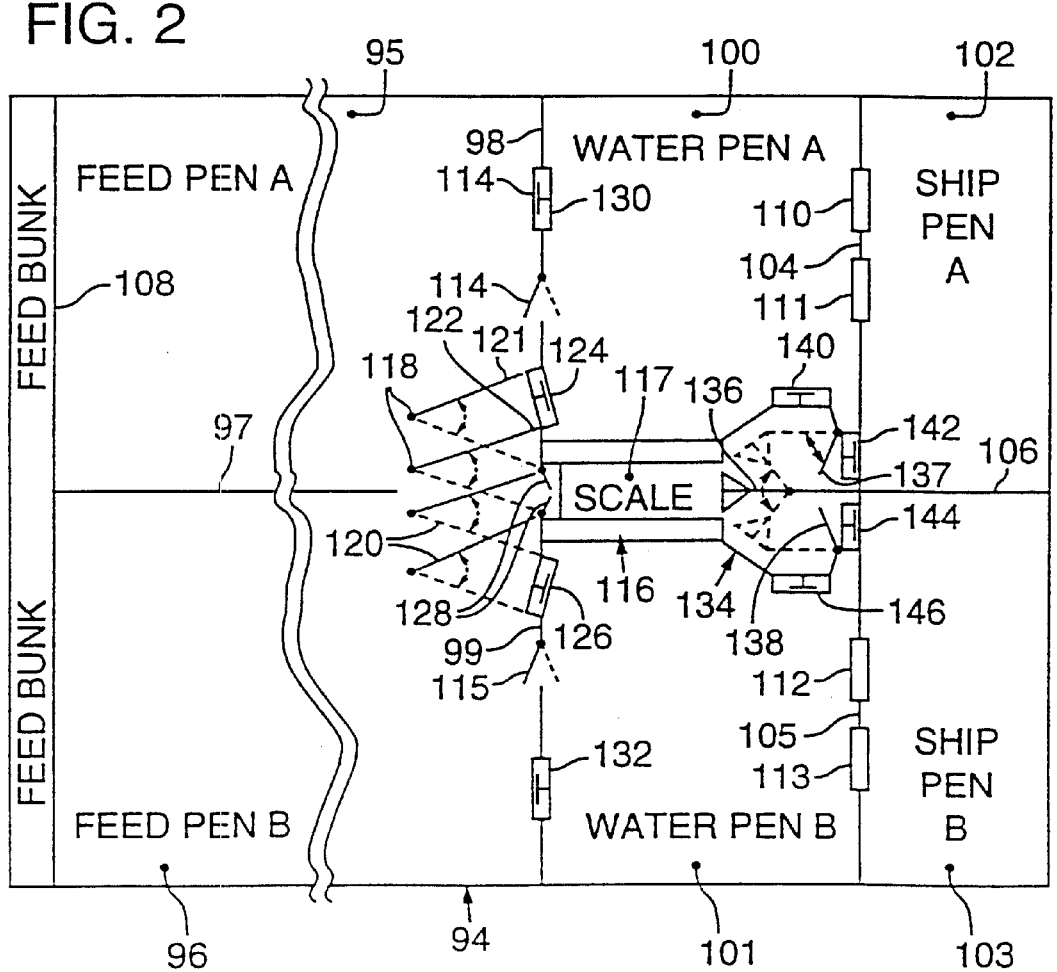
FIG. 2 is a schematic diagram of the layout of a pen sorter including feed pens, water pens and shipping pens for a feedlot in accordance with the invention.

With reference to FIG. 2, a pen sorter 94 is disclosed that is uniquely suited for use as an integral part of the system of the invention and for carrying out the method thereof. There could be one or several pen sorters 94 in a feedlot. It also is possible that the sorting portion of the pen sorter 94, which portion is to be described presently, could be designed as a portable unit that would be transported to a particular feed pen within the feedlot for use there within the 30 days or so prior to scheduled shipment of the group of animals within the feed pen so that the shipment date for each animal in the pen could be optimized for maximum feed efficiency and value.

In any case, the pen sorter is designed to enable weighing of individual animals on a frequent basis, such as daily or even more frequently, without removing the animals from their feed pens and without the need to send them back through the single-file chute described with respect to FIGS. 1 and 5.

The illustrated pen sorter 94 is subdivided into two feed pens 95, 96 designated feed pen A and feed pen B, separated by a partition or fence 97. Each feed pen in turn is also separated by partitions 98, 99 from adjacent water pens 100, 101, designated water pen A and water pen B. Water pens A and B are, in turn, separated from adjacent shipping pens 102, 103 by partitions 104, 105, the shipping pens being designated ship pen A and ship pen B. The ship pens in turn are separated from one another by another fence or partitions 106. Each feed pen includes a feed bunk 108 into which the daily feed ration of the animals in those pens is deposited and to which the animals in the feed pen have ready access. The water pens and ship pens are provided with respective watering troughs 110, 111, 112 and 113 so that the animals within those pens can access drinking water as desired.

The heart of the pen sorter 94 is its array of gates for directing animals in the feed pens A and B to desired locations within the larger confines of the pen sorter 94, on an individual animal basis, based on measured performance characteristics of each animal, other data such as market conditions, and a desired shipping date.

First it should be noted that animals within feed pen A are free to pass between such pen and its adjacent water pen A through a two-way gate 114 to access feed and water as desired. The same is true with respect to animals within feed pen B through a two-way gate 115 between feed pen B and water pen B. However, unless desired by feedlot personnel or dictated by the management system, cattle cannot pass from one feed pen to another or from one water pen to another and cannot pass from either water pen into either shipping pen.

A single scale stall 116 is positioned between water pen A and water pen B and is sized to accept one animal at a time. The scale stall is equipped with one scale at 117 which can be of a type similar to that used in the scale station of the single-file chute as previously described. The scale is set up to transmit automatically the weight reading of an animal through a suitable interface to the host computer. To identify the animal being weighed, the stall also is equipped with an EID tag identification means as previously described for receiving and transmitting the identification of an animal being weighed to the host computer.

Access to the scale stall is either from feed pen A or feed pen B, as desired, through one of two shuttle gates 118, 120. Both shuttle gates 118 and 120 comprise a pair of parallel gate arms 121, 122 which move in unison from a scale entrance position, as shown with respect to shuttle gate 120, to a scale blocking position, as shown with respect to shuttle gate 118 in FIG. 2. When in its scale blocking position, each shuttle gate has its arms 121, 122 directed toward a one-way gate leading into the adjacent water pen. For example, feed pen A shows shuttle gate 118 with its shuttle arms in a position for directing animals through the one-way gate 124 into water pen A. When shuttle gate 120 is in a comparable position, its arms would direct cattle through a one-way gate 126 into water pen B. Thus, depending on the position of shuttle gate 118, animals from feed pen A can be directed either through one-way gate 124 into water pen A or into the scale stall 117. A one-way gate 128 at the entrance to the scale stall prevents an animal that has entered the scale stall from backing out. Similarly, an animal within feed pen B can be directed by shuttle gate 120 either into the scale stall 117 to be weighed or through the one-way gate 126 into water pen B.

Of course, it will apparent that an animal in feed pen A or in feed pen B can at any time pass through the two-way gates 114 and 115 between those pens and their respective water pens A and B, and back again to their respective feed pens. It also will be apparent that any animal within water pen A can also pass through a one-way gate 130 back to feed pen A. However, unless other control gates are operated, an animal in water pen A cannot pass to either shipping pen A or shipping pen B or into feed pen B. Similarly, any animal in water pen B can pass through either the two-way gate 115 or a one-way gate 132 back to feed pen B but cannot pass into shipping pen B, feed pen A or water pen A without operation of appropriate control gates.

Once an animal is within the scale stall 116, it must pass forwardly out of the stall through a complex array of sorting gates indicated generally at 134 into one of four pens, either water pen A, shipping pen A, water pen B, or shipping pen B. The operation of the sorting gate array 134 is under computer control. The scale stall 116 is provided with an EID tag antenna to identify the animal within the scale stall to the computer system, which then determines which pen the animal is to proceed to from the scale stall, after which the computer operates the sorting gate array 134 in a manner to direct the animal to the appropriate pen.

Sorting gate array 134 includes three controllable shuttle gates 136, 137 and 138. In addition, it includes a one-way gate 140 leading from the sorting area just downstream from the scale stall into water pen A, a one-way gate 142 leading from the same sorting area into shipping pen A, a third one-way gate 144 leading from the sorting area into shipping pen B and a fourth one-way gate 146 leading from the sorting area into water pen B.

The following will illustrate that an animal in, for example, feed pen A can be directed through the scale stall 116 and then either back to feed pen A, to feed pen B, to shipping pen A or to shipping pen B. The same is true with respect to an animal in feed pen B. Thus, pen sorter 94 is capable of effecting a four-way sort.

To illustrate, an animal in feed pen A with the shuttle gate 118 in the position shown, can pass freely between feed pen A and water pen A and back to feed pen A. However, with the shuttle gate 118 shifted to its position shown in dashed lines in FIG. 2, an animal in feed pen A will be directed through the one-way gate 128 into the scale stall 116 where it will be weighed and identified to the computer through its EID tag. The computer will then determine to which pen it should be sorted from the scale stall and actuate the appropriate gates to accomplish the desired sort. For example, if it is desired to return the animal to feed pen A, sorting gate 136 is shifted downward to its dashed line position shown thereby allowing the animal to move through the sorting area and through the one-way gate 140 back to water pen A where it can move freely back to feed pen A, either through the two-way gate 114 or the one-way gate 130.

If it is desired that the animal be sorted from feed pen A to feed pen B, sort gate 136 is shifted upward to its dashed line position shown, allowing the animal to travel from the scale stall freely through the sorting area and one-way gate 146 to water pen B, from which the animal can move freely through either two-way gate 115 or one-way gate 132 to feed pen B.

If it is desired that the animal move from the scale stall 116 to shipping pen A, sort gate 136 is moved to its downward position in FIG. 2 and control gate 137 is moved to its upward position shown in dashed lines in FIG. 2, enabling the animal to travel through the sorting area and through one-way gate 142 into shipping pen A.

If it is desired that the animal move from the scale stall to shipping pen B, sorting gate 136 is moved upward, control gate 138 is moved downward to its dashed line position, and the animal can thus move freely through the sorting area and one-way gate 144 into shipping pen B.

From the foregoing it will be understood that animals within feed pens A and B can be weighed as frequently as desired and sorted four ways without moving the animals any appreciable distance. Thus the pen sorter 94 provides an ideal finishing pen for use in determining the exact day within a shipping window of several days when an animal should be shipped to the packing plant for slaughter to realize the maximum return on the investment in such animal, considering animal performance, market conditions and feed efficiency.

B. Cattle Management System and Process

Figure 3:
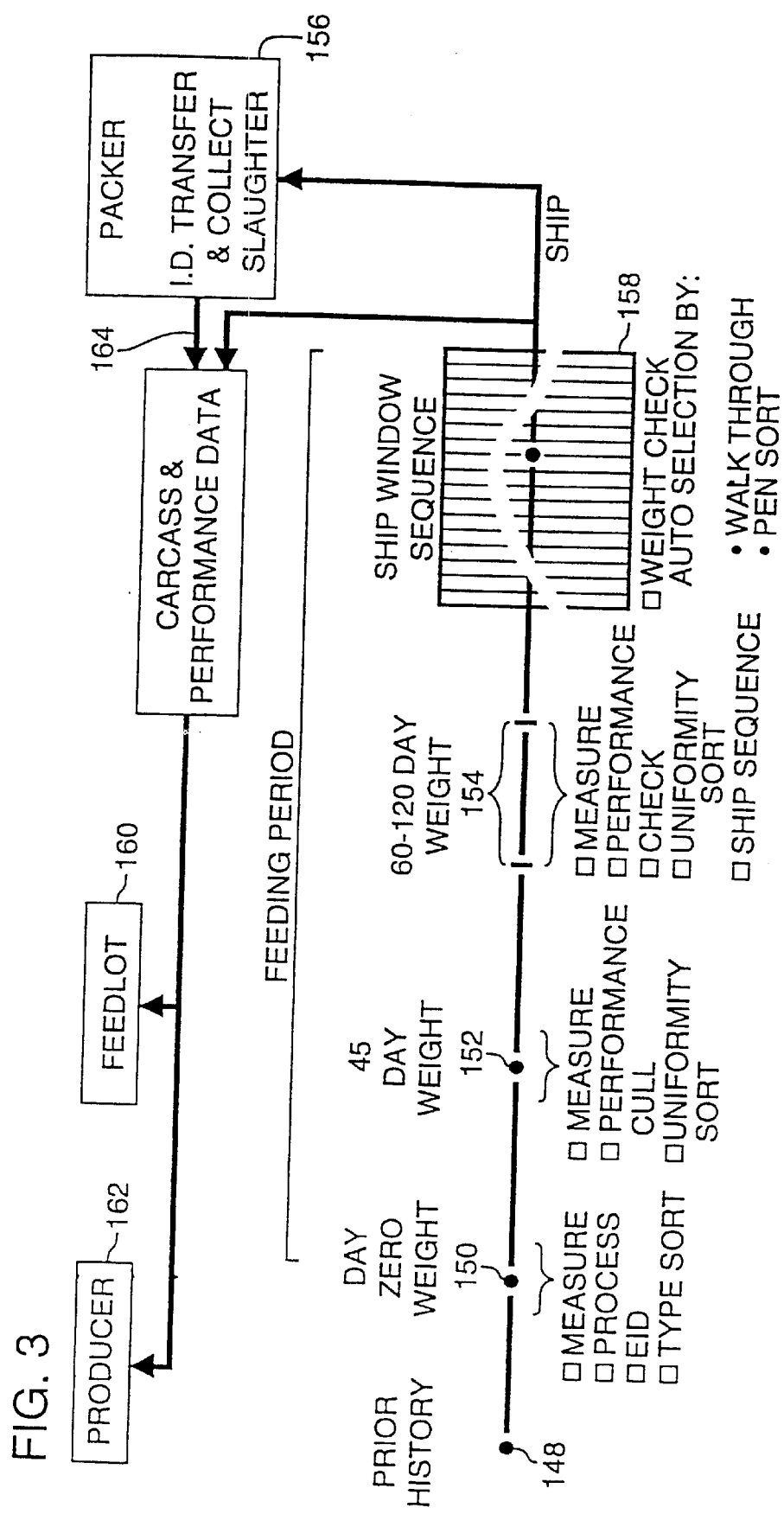
FIG. 3 is a cattle-processing timeline to exemplify a method of processing and managing cattle in accordance with the invention.

FIG. 3 illustrates a hypothetical timeline in the management of cattle in accordance with the invention.

Upon arrival of a lot of cattle in the feedlot, or before, the prior history of the lot would be entered in the host computer 78, as indicated at 148. Such prior history data is illustrated, for example, in the cattle received report by "load" shown in FIG. 9A. The report indicates such things as the date the load was received, the load number, the number of head in the load, the sex of the cattle in the load and the average weight of the animals in the load. It also indicates cost information. It also gives information, such as the age of the cattle, the breed, the type of pasture the load has been on and health, nutrition, stress and weather conditions applicable to the load. It also indicates the number of days the load has been feeding on pasture. Some or all of this data may be used in later calculations by the computer to determine the optimum end date (OED) or days to finish (DTF), of the group or individual animals in the group. This date is also sometimes referred to as the optimum marketing or shipping date.

On the day of their arrival, indicated on the timeline at 150, each animal in the load is measured, processed and electronically identified with an EID tag in the one-way single-file chute 22 previously described. Then, if desired, the measured and processed animals may be sorted into the sorting pens 30 in a rough sort by type (breed), weight, age, or a first estimated OED or DTF, although such a first "rough" first sort is optional.

From the sorting pens, the animals are moved to feed pens, either by sort or on an ad hoc basis, where they are fed for a period of time, such as 45 days as shown in FIG. 3, although possibly substantially longer than that.

If a 45-day weight or measurement is desired for the animals, they would be moved from their feed pens on the 45th day as indicated at 152 back through the single-file chute, where they would be remeasured. From the initial measurement and remeasurement data, the performance of each animal would be calculated by the computer, and its performance assessed. The animals would then be sorted into the sorting pens 30 according to their performance characteristics. Poorly performing animals would be culled from the group and removed from the feedlot operation as "salvage". The remaining resorted animals would be returned to the feed pens according to their sorts.

Then 60–120 days into the feeding period, indicated by the range 154 in FIG. 3, the animals from at least two feed pens at once would be moved from their pens back through the single-file chute for remeasuring once again on an individual basis. The data from these measurements together with prior data for each animal would be used by the computer to calculate a new OED or DTF for each animal and other performance criteria, such as average daily gain (ADG) and feed proration for each animal. From the single-file chute, the animals would be resorted once again according to predetermined criteria such as DTF or OED. A projected shipping sequence for each animal could also be calculated at this time. Then the animals would be returned to the feed pens according to the newly determined sorts. The animals then could be removed from their pens for shipment according to their calculated shipping sequence. Whenever an animal is moved in the feedlot, its identification and data, via computer, moves with it. Its location at any time can be determined remotely by computer, and its performance data assessed.

Alternatively, a portable pen sorter of the type shown in FIG. 2 could be installed in the feed pen. Each animal would be carefully monitored and weighed, perhaps on a daily basis, until it reached its optimum shipping weight or value, at which time it would be shipped to the packer, indicated at 156.

Alternatively, animals within the feed pens could be sent to a finishing pen such as the pen sorter 94 shown on FIG. 2 where it would be confined, monitored and weighed frequently within a shipping window such as a 30 day shipping window. Within that shipping window indicated at 158, each animal as determined by frequent weight checks and market conditions, would be directed from its feed pen, such as feed pen A or feed pen B in FIG. 2, to appropriate shipping pen A or B when it is ready for shipment.

Alternatively, during an animal's shipping window, the animal could be weight checked simply by sending it back through the single-file chute periodically until it reaches its ideal shipping weight, at which time it would be shipped to the packer 156.

Alternatively, a specific shipping date for a given animal could be determined by issued inspection while the animals are within their 30-day shipping window.

When the animal leaves the feedlot, its EID tag travels with it. Its historical and performance data records would be maintained by the feedlot, indicated at 160, and also transmitted to the producer, indicated at 162. At the same time, the packer would record the carcass data for each slaughtered animal, identified by its EID tag, and transmit the carcass data, as indicated at 164, to the feedlot and producer for correlation with the animal's live performance data from the feedlot.

The correlation can be useful to the feedlot in projecting optimum end dates (OED), initial feed proration and production costs for future animals of a given type and similar history. This data also can be useful to cattle producers in determining which breeds and individual-breeding animals are most desirable from the standpoint of market value and producing the best quality of beef. The important thing to note is that the performance of each animal is tracked on an individual basis from the time it arrives in the feedlot until the time it is shipped and slaughtered, when its carcass data is collected and correlated with its performance data for use by the feedlot and producer in managing future beef production.

Another important feature of the system is its ability to update an individual animal's performance projections on a daily basis. For example, the DTF for an animal will be current for the day the projection is assessed. The same is true for other projections such as projected weight, etc.

Although FIG. 3 illustrates one possible processing sequence of cattle including measuring and remeasuring steps and sorting and resorting steps for optimum feed efficiency and return, many other sequences are possible as illustrated in FIGS. 4A, 4B and 4C. For example in the sequences of FIGS. 4A, 4B and 4C the 45-day remeasurement is eliminated and instead a single 60–75 day remeasurement and uniformity sort are performed.

Referring to FIG. 4A, a load of cattle is received in the feedlot at 166 and within a few hours, measured at 167 and processed at 168 in the single-file chute. From the chute, they are directed into the feed pens at 169 without an initial sort. They are fed in the feed pens for 60–75 days, then returned to the single-file chute for remeasuring at 170 and possibly reimplantation of a growth hormone, if necessary. After remeasuring, the animals undergo a uniformity sort as determined by the computer, and directed into the appropriate sorting pens 172. Upon completion of the sorting operation, they are returned to the feeding pens 174 according to their sort groups and there fed for a period of 60 to 80 days. As the cattle within the feed pens approach their individual optimum end dates they would be selected for shipment either visually, by remeasurement at the single-file chute, or by frequent reweighing in a portable pen sorter of the type shown in FIG. 2. Following selection at step 176 the animal would be shipped as at 178 to the packer.

The processing sequence of FIG. 4B for an individual animal is the same down through the initial receiving, measuring and processing steps. However after measuring and processing, according to FIG. 4B there is an initial sort step 180 that can be a rough type sort as in FIG. 3 or can be based on a first rough estimated optimum end date for each individual animal. Following the first sort 180, the animals are directed by sort group into feed pens at 169 for a feeding period of 60–75 days. At the end of the 60–75 day period the animals are removed from their pens, either individually or in-groups, and returned to the single-file chute for remeasuring at 170.

After remeasuring in the single-file chute, each animal is resorted at 182 by the computer, which opens the appropriate sorting gates of the sorting pens 30. From the sorting pens, the animals are redirected back to the feed pens at 174 and placed into the pens according to their sorting groups. They remain in the feed pens for a period of 60–80 days, after which they are individually, or by group, selected for shipment, according to their last calculated OED. As previously indicated, this selection for shipment can be fine-tuned through the use of either a portable pen sorter or the pen sorter 94 of FIG. 2. After selection, the selected animals are shipped at step 178 to the packing plant for slaughter, where the carcass data and EID tag are collected.

The optional cattle processing procedure of FIG. 4C is the same as the procedure outlined in FIG. 4A down through the initial sorting step 172. However, thereafter the animals, according to the procedure in FIG. 4c, are directed back to the feed pens according to sorting group at step 173 for a feeding period of only 30–40 days. Thereafter, the animals, or at least selected animals, from the feed pens are removed to finish feed pens, such as pen sorters 94 in FIG. 2, for a finish feeding step 175 for an additional 30–40 days, which represents the shipping window 158 indicated in FIG. 3. Within the finish feeding pens, the animals can be sorted, resorted, weighed, reweighed and selected on an individual animal basis for sorting to one of the two shipping pens A and B for shipment to the packer at step 178.

C. Cattle Processing Example

Figure 7:
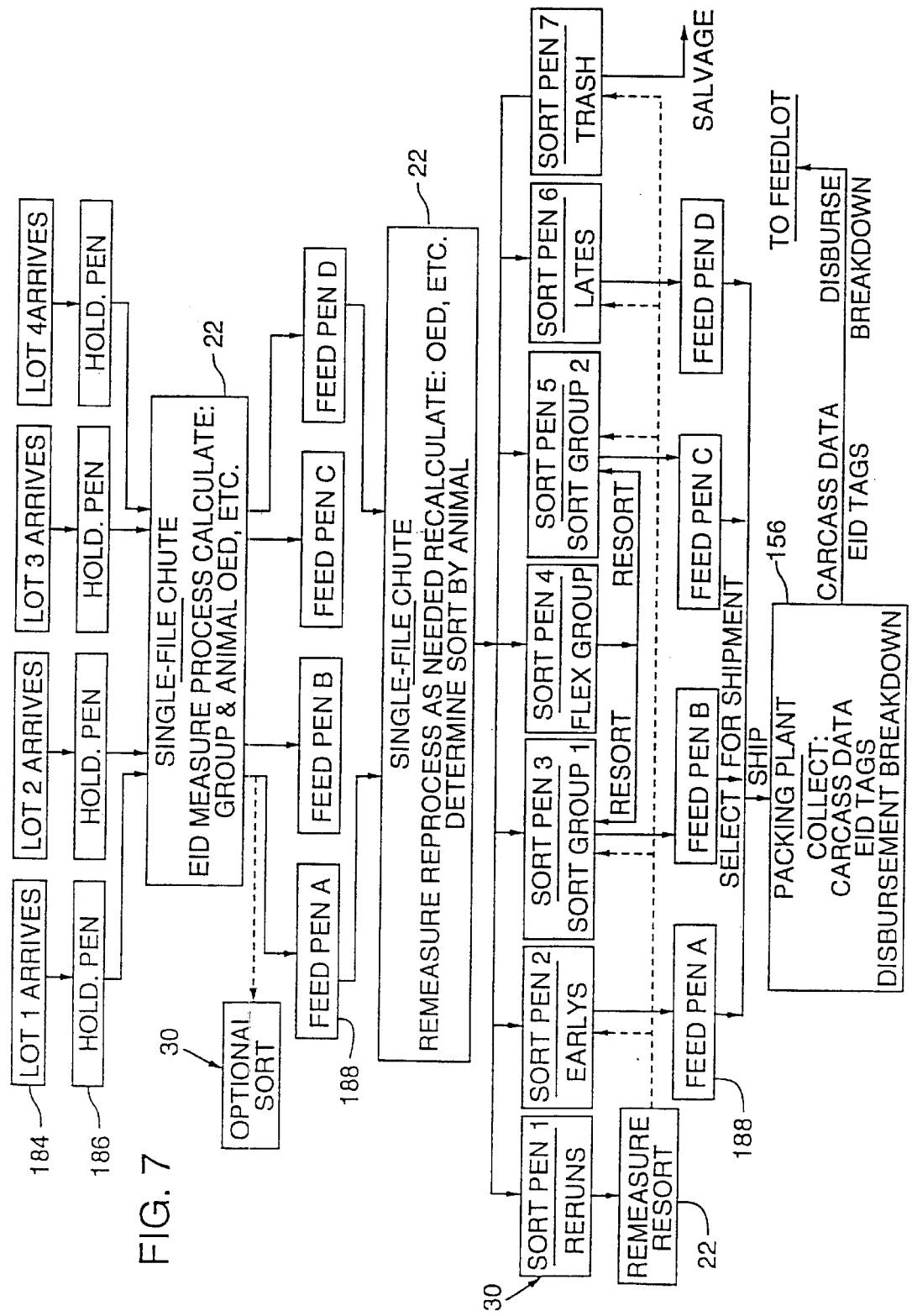
FIG. 7 is a cattle processing diagram but in considerably greater detail than those of FIGS. 4A, 4B and 4C to illustrate a method of the present invention.

FIG. 7 illustrates, in greater detail, a representative cattle processing sequence in a feedlot according to the system and process of the present invention. Steps in the processing sequence are numbered 19 along the left-hand side of FIG. 7.

In step 1, as indicated at 184, several lots of cattle arrive at the feedlot at about the same time, indicated as lots 1. When they arrive, the previous history data of the lots and individual animals in the lots is entered into the host computer by data entry means (not shown) such as a computer keyboard.

Figure 8:
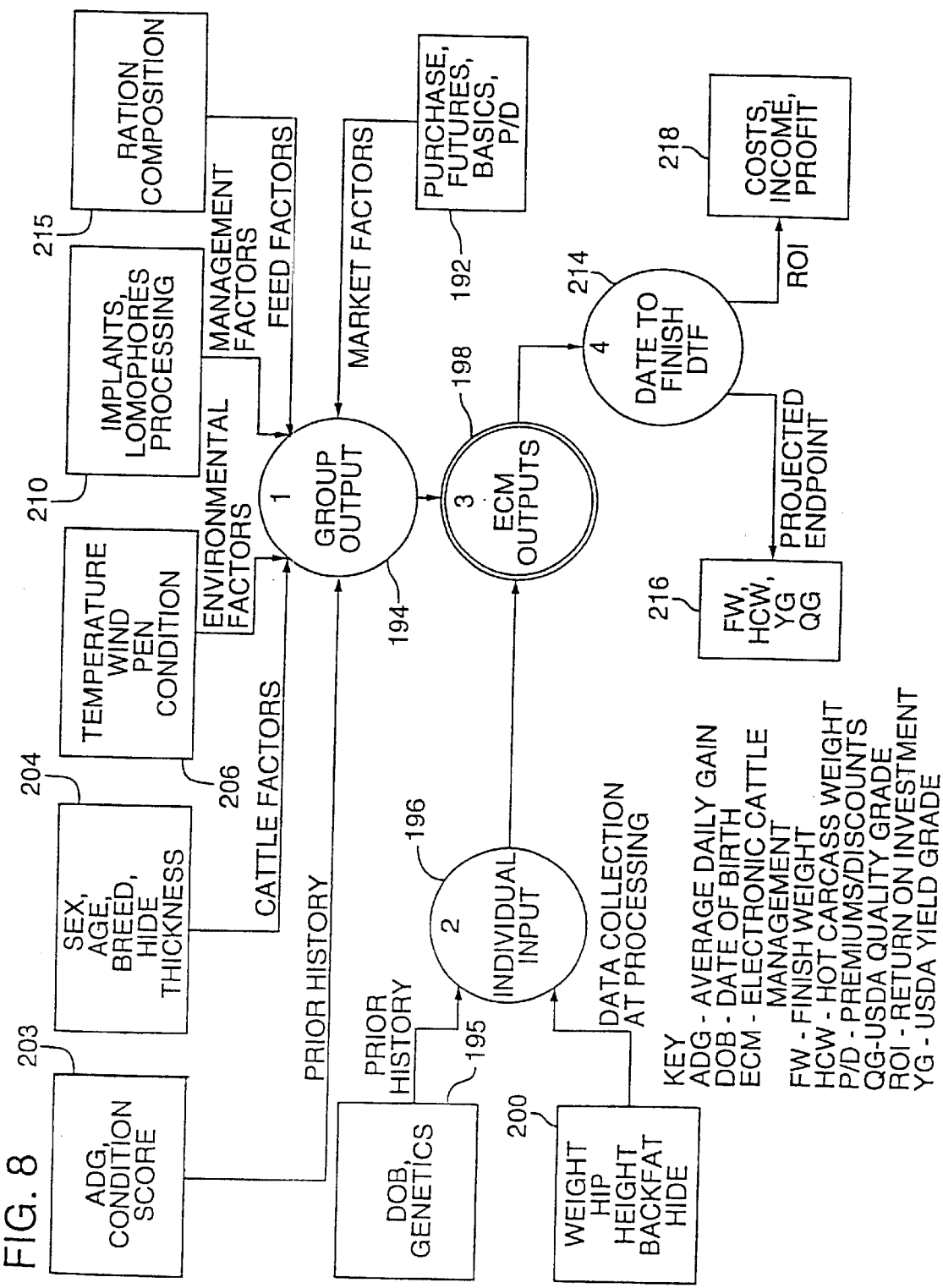
FIG. 8 is a data flow block diagram illustrating the data flow in a computerized control system according to the present invention.

FIG. 8 is a general block diagram of the data inputs and data outputs to the host computer system 78. There are two categories of inputs, including the group-input category 194 and the individual animal input represented by interface 196. The individual prior history of each animal is entered upon each animal's arrival at the feedlot, as indicated by the prior history input 198. Such prior history would include each animal's date of birth and its genetic background. Also entered at initial processing and on subsequent remeasurements would be each animal's weight, hip height, backfat and hide condition as indicated at input 200. These measurements are obtained at the single-file chute in the manner previously described. These individual inputs in turn are transmitted by cable or radio frequency means to the host computer 78 for storage and use in calculating the previously discussed formulas. Group information when transmitted to the computer would include prior history data such as average daily gain while in the pasture and the group condition score, visually estimated at the time of arrival at the feedlot. Other information would include the sex, age, breed and hide thickness breakdown for the animals in the group. These "cattle factors" are also input into the computer through data entry means indicated at 204 and the group input interfaces 194.

Environmental factors such as air temperature, wind, and pen conditions where the animals came from are also collected and entered through data entry means 206 into the group input interface 194.

Management factors for each group including implants, ionophores and processing information, are collected and input through data entry means 208 into the computer through the group input interfaces 194. Finally, feed factors, such as ration composition, are input through data entry means 210 and the group input interfaces 194 into the host computer 78.

Market factors are also part of the data used to calculate the desired computer outputs, such factors including purchase price, cattle futures, basis and premium/discounts for the animals in the group. These market factors are entered through data entry means 192 and the group input interface 194 into the host computer 78.

With the data collected as described, and the appropriate software, the computer system is able to calculate, using formulas such as the ones described in Pratt's U.S. Pat. No. 5,673,647, such outputs as a projected date to finish (DTF), optimum end weight (OEW), and projected end points such as finish weight, hot carcass weight, yield grade, and USDA quality grade. The computer system also calculates a return on investment including cost, incomes and profit as indicated at 218.

Figure 6:
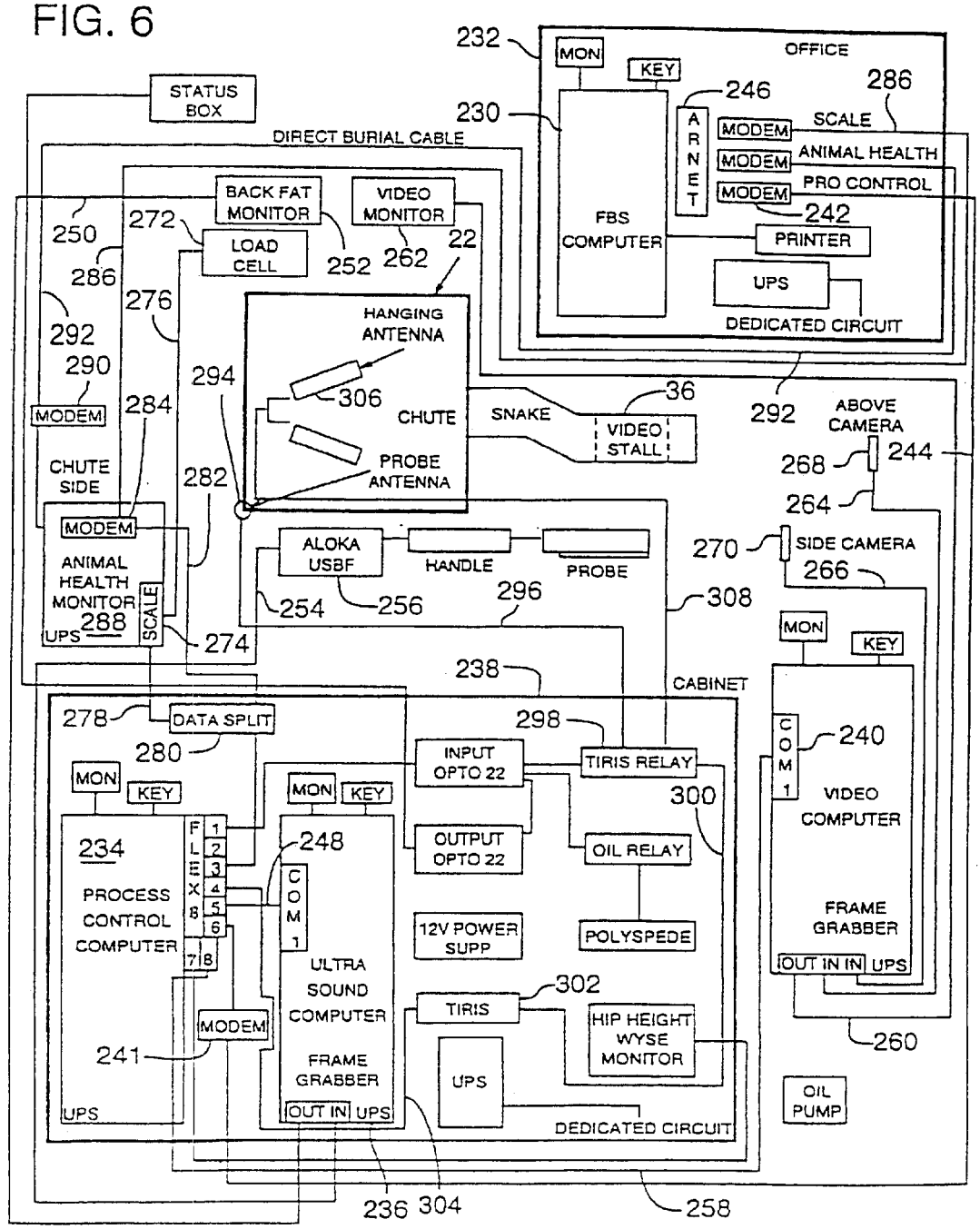
FIG. 6 is a block diagram of the computerized control system that may be used for carrying out the present invention.

A layout of the computer system used in a prototype of the present invention is shown in FIG. 6. Several different computers are used in the system. First, there is a feedlot business systems (FBS) computer 230 located at the feedlot office 232. This computer stores the databases used in the system and performs most of the calculations needed in operating the system.

Remote from the FBS computer and closer to the chute area 22 are a separate process control computer 234 and an ultrasound computer 236 within a common control cabinet 238. Separate from the control cabinet and the other computers is a video computer 240.

Basically, the process control computer 234 controls the operation of all subsystems including the stall and sorting gates, weigh scale, ultrasound computer and the video computer. The process control computer communicates with the FBS computer through the modems 241, 242, line 244 and FBS interface 246. The ultrasound computer 236 communicates with the process control computer 234 through a line 248. The ultrasound computer 240 also has an output line 250 to a backfat monitor 252 and an input line 254 from the ultrasound backfat scanner 256 at the single-file chute stall 40.

The video computer 240 communicates with the process control computer 234 through a commline 258. It also has an output line 260 to a video monitor 262, and input lines 264, 266 to video cameras, including an overhead camera 268 and a side-view camera 270.

Each animal is weighed by a scale loadcell 272 at the weigh stall 38. The loadcell communicates with the scale 274 through a line 276. The scale in turn communicates with the process control computer through a line 278 and data split 280. Data from the data split also can be communicated via line 282 and a modem 284 and line 286 directly to the FBS computer 230 through the FBS interface 246.

Data concerning drugs, other animal health treatments and other information about an individual animal at the processing station or stall 42 can be entered into an animal health computer or monitor 288 at the processing station and from there communicated directly through the modem 290 and line 292 and interface 246 to the FBS computer.

As previously noted, each animal has an EID tag applied to it in the single-file chute to give each animal a unique electronic identification. This identification is transmitted from the EID tag by a probe antenna 294 at the EID/USBF stall 40 through a line 296 from the chute to a tiris relay 298 and from the relay through a line 300 to a tiris EID reader 302. The tiris reader 302 transmits the animal's EID identification through a line 304 to the process control computer 234. Alternatively, each animal's EID tag signal can be received by a hanging antenna 306 at the single-file chute and transmitted via line 308 to the tiris relay 298 and thence through line 300 to the tiris reader 302 and through the line 304 to the process control computer 234.

The FBS computer not only collects data and uses it to calculate projections, costs and other information used in the management method and system, it also collects data from other sources not shown. For example, the FBS computer performs the regular feedlot accounting functions and generates financial reports. It may also receive and store data from a computerized animal drug inventory control and animal health history and drug treatment system as disclosed in the previously mentioned U.S. Pat. No. 5,315,505. The FBS computer may also collect and store data from a computerized feed additive delivery system such as disclosed in U.S. Pat. No. 4,733,971 and the related patents previously mentioned. The FBS computer may also receive and store data concerning the amount of feed ration delivered to each of the feed pens in a feedlot, including such data collected from a computerized bunk reader system such as disclosed in U.S. Pat. No. 5,008,821. All such information, including the drug usage information, feed ration usage information, and feed additive usage information can be used together with the data concerning each animal collected from the system of the present invention and other data that may be collected and stored in the FBS computer database to prorate feed ration and feed additive costs to individual animals and thereby calculate the cost of production value and other pertinent information about each animal in the feedlot according to various formulas, a few of which are disclosed as examples and discussed.

II. Ultrasound Tissue Imaging and Analysis Device

A. Electric and Fluid Line Connection

Figure 9:
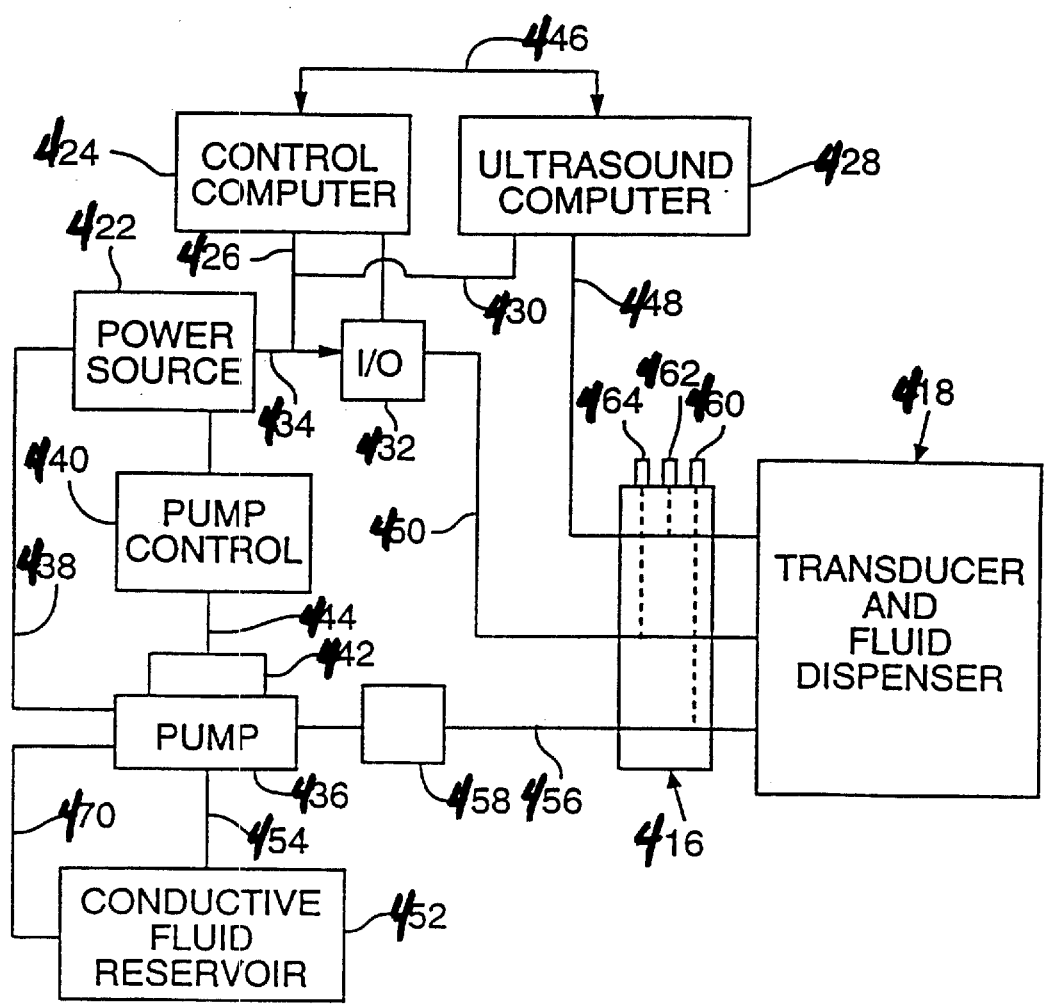
FIG. 9 is a schematic diagram showing a complete system of one embodiment of an ultrasound tissue imaging and analysis apparatus.

FIG. 9 is a block diagram, which illustrates certain components for an embodiment of the present invention. FIG. 9 also illustrates certain fluid and electric interconnections between these components. The illustrated embodiment includes switch unit 416 and handpiece 418. A monitor 420 (not shown) also is used. Power source 422 is electrically coupled to each unit requiring power. More specifically, power source 422 is electrically coupled to control computer 424 by cable 426, to ultrasound computer 428 by cable 430, to input/output module 432 by cable 434, and to pump 436 using cable 438. Pump 436 is controlled by pump control 440, which is electrically coupled to a three-way solenoid valve 442 by cable 444. A data cable 446 interconnects control computer 424 and ultrasound computer 428. FIG. 9 also illustrates that the ultrasound computer 428 is electrically coupled to switch unit 416 by cable 448. Input/output module 432 also is electrically coupled to the handpiece 418 by cable 450.

Pump 436 is fluidly coupled to reservoir 452, which contains a conductive fluid, by fluid conduit 454. Pump 436 is further fluidly coupled to switch unit 416 by fluid line 456. As shown in FIG. 9, a quick disconnect 458 may be placed in fluid line 456. This quick disconnect 458 is provided solely for convenience, and allows the pump fluid line 456 to be quickly disconnected from handpiece 418.

Each of the individual lines, namely electric cables 448, 450, and fluid line 456, are interfaced with the handpiece 418 by switch unit 416. Each of the components of the apparatus can be individually actuated using the switches 460, 462 and 464 on switch unit 416. Thus, by depressing the appropriate switch, each function of the apparatus can be actuated.

B. Components of a Working Embodiment

The components of the apparatus mentioned above will now be described in more detail. Power source 422 is a conventional piece of equipment that can be obtained commercially. Virtually any power source now known or hereafter developed that can safely power sensitive electronic apparatuses can be used to practice the invention.

Control computer 424 also is a conventional piece of equipment, and any computer which has sufficient capability to control and interface with ultrasound computer 428 will suffice. One example, without limitation, of a control computer 424 suitable for this operation is an IBM PC. Control computer 424 controls certain functions of the ultrasound computer 428. Commercial software is available for operating the control computer 424 to control ultrasound computer 428. One example of software suitable for this operation is sold by Animal Ultrasound Services, Inc., of Ithaca, N.Y.

The present apparatus operates by generating and transmitting into livestock an ultrasound energy pulse. This energy pulse is produced and controlled by ultrasound computer 428 and ultrasound transducer 466. Each of these components can be purchased. One example of an ultrasound apparatus that can be used to practice the invention is an ALOKA 500 V Ultrasound Computer. The ALOKA 500 V is purchased in combination with an ultrasound transducer 466 and transducer cable 468 for coupling the transducer 466 to the computer 428.

Input/output module 432 controls the signals input to and from computer 424 and to the components housed in handpiece 418. Again, the I/O module 432 is a conventional piece of equipment, and virtually any input/output module 432 will suffice for this invention. One prototype of the invention was assembled using an OPTO 22 I/O board. The OPTO 22 I/O board includes: a 1AC5Q input module; a PB16HQ circuit board; a B1 brainboard; a PBSA PP/S power supply; and an OAC5Q output module.

A pump 436 pumps conductive liquid to handpiece 418. The conductive liquid is contained in reservoir 452. Any conductive liquid likely will work for the present invention. The selection of a suitable conductive liquid will best be decided by considering, inter alia, the conductivity of the liquid, the expense of the liquid, the availability of the liquid and the toxicity of the liquid. Solely by way of example, suitable conductive liquids may be selected from the group of conductive liquids consisting of water, vegetable oil and mineral oil. Pump 436 is liquidly connected to conductive liquid reservoir 452 using liquid conduit 454, which was made from flexible TIGON tubing. A pressure equalization tube 470, also made from TIGON tubing, couples the liquid reservoir 452 and the pump 436. Pressure equalization tube 470 equalizes the pressure between the pump 436 and the reservoir 452 when the pump 436 is not in operation. This helps prevent liquid leaks from reservoir 452.

Conductive liquid is dispensed from reservoir 452 upon actuation of the pump 436. Liquid dispensation is controlled by a three-way solenoid valve 442, which is electrically coupled to pump control 440. Three-way valve 442 can be electrically actuated by switch 460, which is housed in switch unit 416. This dispenses conductive liquid from reservoir 452 through liquid conduits 454 and 456 to handpiece 418. When the pump 436 is not in use, the solenoid valve is open to pressure equalization tube 470 to equalize the pressure between the pump 436 and reservoir 452.

Liquid back flow from handpiece 418 can be checked by a check valve 472, which is mechanically coupled to the handpiece 418.

Figure 10:
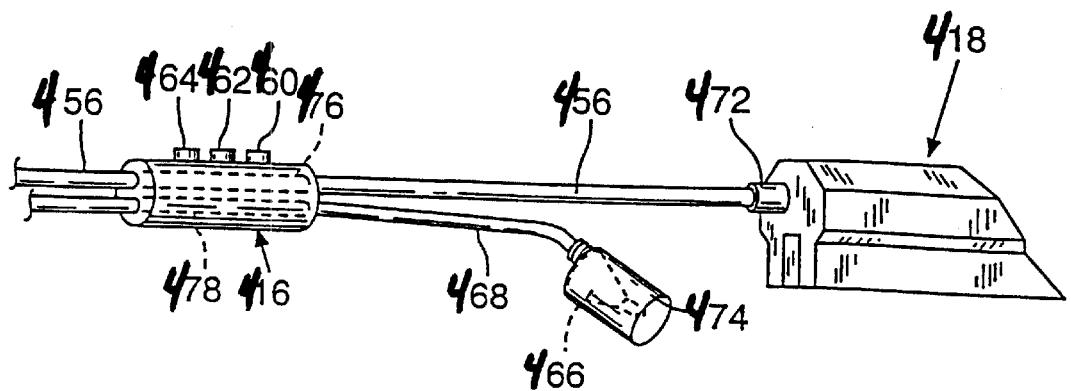
FIG. 10 is a side, partially disassembled view, illustrating an ultrasound transducer and dispensing handpiece unit of the invention.

FIG. 10 is a schematic diagram of the switch unit 416, handpiece 418, cables 448, 450, and liquid conduit 456. FIG. 10 shows transducer 466 separated from handpiece 418. FIG. 10 further shows that ultrasound transducer 466 is surrounded by a clear protective housing 474. Housing 474 performs at least two functions. First, housing 474 protects ultrasound transducer 466 from contact damage. Furthermore, protective-housing 474 facilitates the positioning of transducer 466 in handpiece 418 as described below. The protective housing 474 in a prototype illustrated in FIG. 10 was made from TIGON tubing sized to tightly receive transducer 466 therein.

Figure 11:
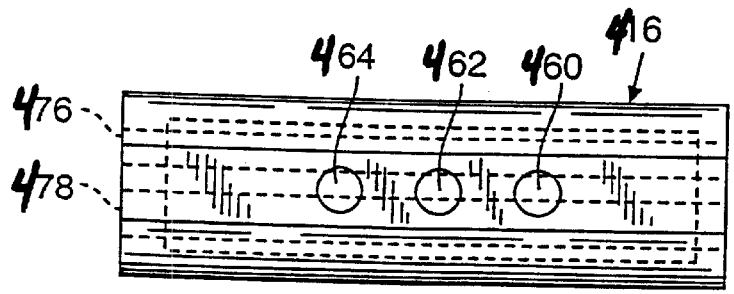
FIG. 11 is a plan view of the switch unit illustrated in FIG. 10.
Figure 12:
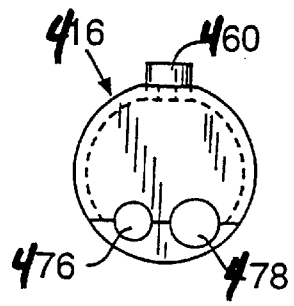
FIG. 12 is a front-end view of the switch unit of FIG. 11.
Figure 16:
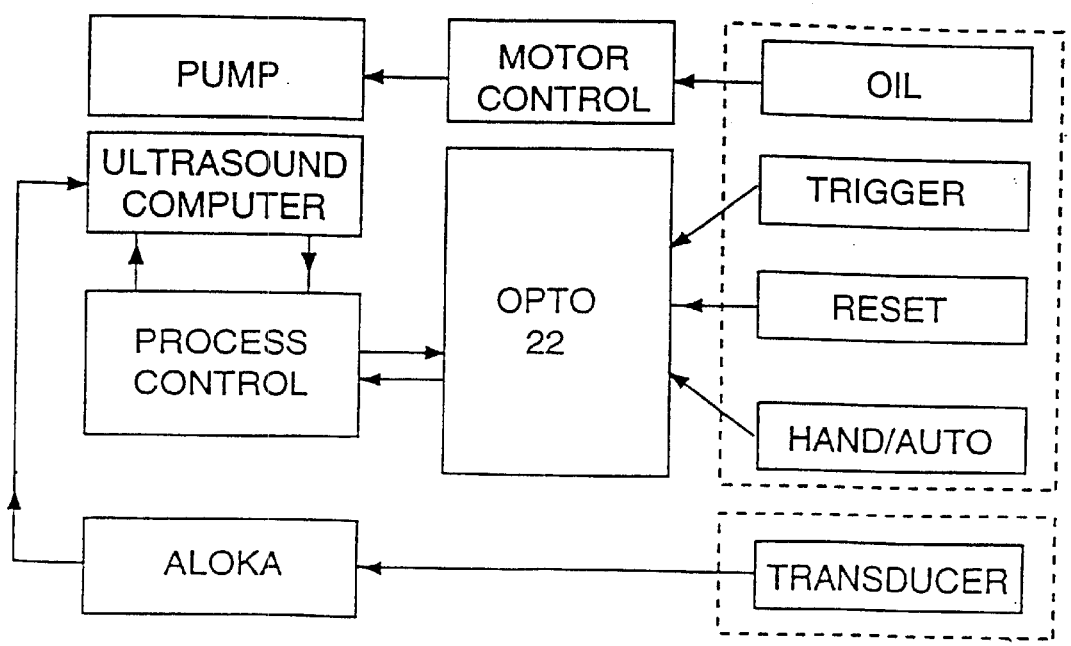
FIG. 16 is a schematic illustrating the switch unit of FIG. 11.

FIG. 11 is a schematic top plan view and FIG. 12 is an end view illustrating switch unit 416. In a prototype, switch unit 416 was made from a polypropylene block that was machined to include passages 476 and 478 therethrough. Conduit 476 provides a passage through switch unit 416 for liquid line 456. Passage 478 provides a passage through switch unit 416 for electric cables 448 and 450. Switch unit 416 includes three switches 460, 462 and 464. The switches include conductive liquid switch 460, trigger switch 462 for commanding the computer to read and analyze the image, and reset switch 464 for clearing a previous reading to prepare for rereading an animal or reading a new animal. These switches and their functions also are illustrated in FIG. 16. Switch 460 actuates liquid pump 436 so that conductive liquid from reservoir 452 is pumped through liquid line 456 and into handpiece 418. The amount of time that pump 436 operates is governed by a timer switch on pump 436 (not shown). Thus, by actuating switch 460, pump 436 is induced to pump conductive liquid from reservoir 452 for the period of time allowed by the timer switch on the pump. In a current prototype, the pump 436 is actuated for a period of less than about 5 seconds, and typically about 3 seconds, during which time less than about 50 milliliters, and more typically about 30 milliliters, is pumped from reservoir 452 to the handpiece 418.

A second switch 462 is electrically coupled to the ultrasound computer 428 by cable 448. Switch 462 activates the computer 428 to read and analyze the ultrasound image that is produced by transducer 466 as displayed on monitor 420. Thus, once the transducer 466 is correctly positioned, operator 414 depresses switch 462 to cause the computer 428 to read the ultrasound image.

A third switch 464 also is provided on switch unit 416. Switch 464 is a reset switch electrically coupled to input/output module 432 by cable 450. Switch 464 is depressed by operator 414 when the image has been read by computer 428 or when the operator wants to discard a previous reading and record a new reading of a given animal's image. This can include reapplying conductive liquid from the handpiece 418 onto the animal. This resets the computer 424 and input/output module 432 for receiving new information from a different animal 410.

Figure 13:
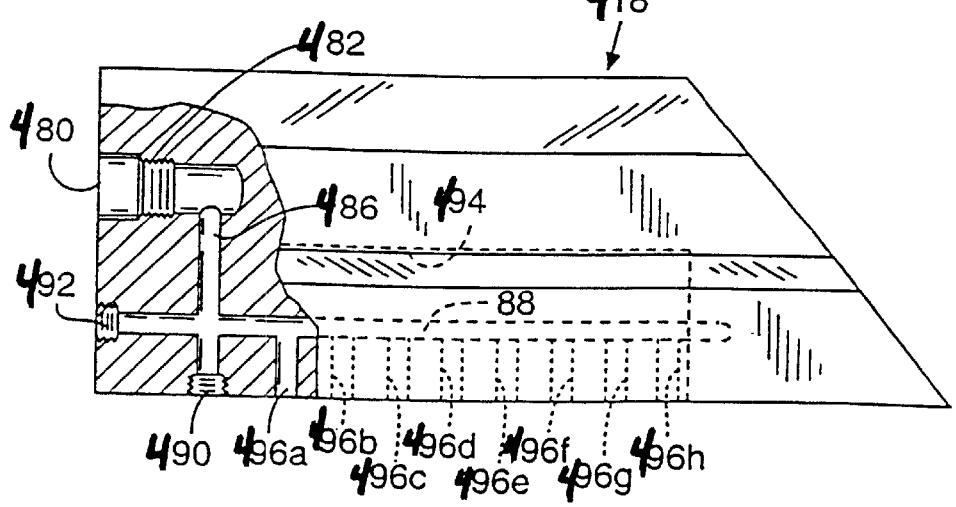
FIG. 13 is an enlarged side view of the handpiece illustrated in FIG. 10.
Figure 14:
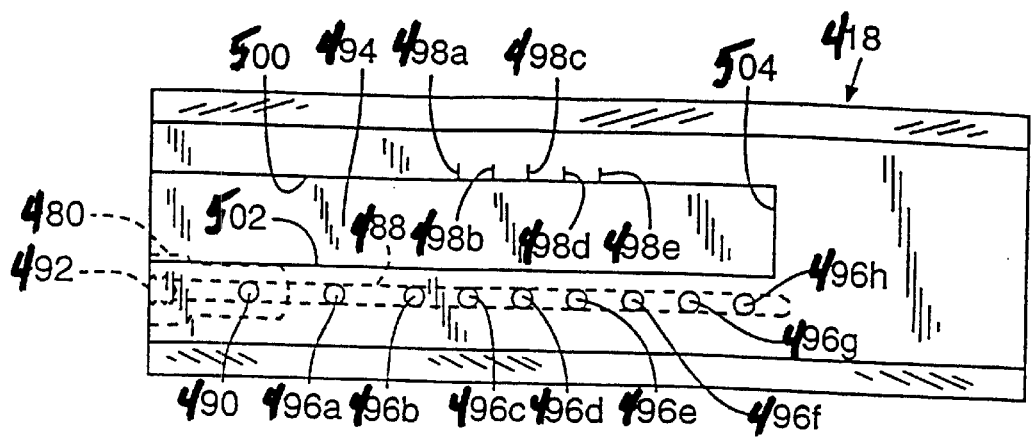
FIG. 14 is a bottom plan view of the handpiece of FIG. 10.

FIGS. 12–14 further illustrate the construction of handpiece 418. FIG. 13 is a side schematic view of the housing 418. Housing 418 is manufactured for this particular application, and can be manufactured from a number of suitable materials. The embodiment of a prototype illustrated in FIGS. 12–14 was manufactured from polypropylene. A block of polypropylene having suitable dimensions was obtained and then machined to have substantially the appearance illustrated in FIGS. 12–14.

More particularly, handpiece 418 is machined to include a threaded inlet 480 for receiving liquid line 456. Any suitable means for coupling the liquid line 456 to housing 418 will suffice. FIGS. 12–14 illustrate a male threaded connection 482 which is inserted into threaded portion 484 of passage 480 to couple liquid line 456 to housing 418. Housing 418 also is machined to include a passage 486 for interconnecting liquid inlet 480 and a liquid conduit 488. Liquid conduit 486 is closed using a threaded plug 490, and liquid conduit 488 is closed by a threaded plug 492.

Figure 15:
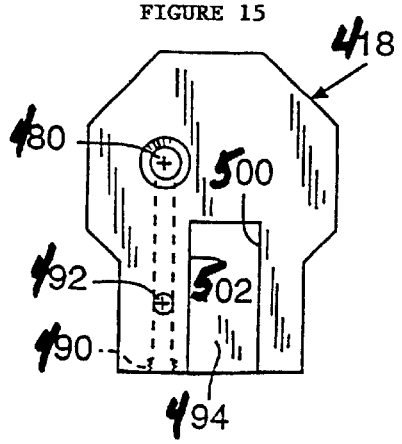
FIG. 15 is a rear end view of the handpiece illustrated in FIG. 10.

FIG. 14 is a bottom plan view and FIG. 15 is an end view of the handpiece 418. FIGS. 14 and 15 illustrate a longitudinal slot 494 recessed in the bottom surface of the handpiece 418. Slot 494 is sized to receive the transducer 466 and protective cover 474. If, however, the transducer 466 and cover 474 are not received sufficiently tightly in slot 494 to hold the ultrasound transducer 466 securely therein, an additional polypropylene wedge (not shown) can be used to wedge ultrasound transducer 466 and protective cover 474 inside the slot 494.

FIG. 14 also illustrates that leading to and intersecting with the conduit 488 are plural output orifices 496a–496h. These orifices 496a–496h are fed by liquid line 456. Thus, as a conductive liquid enters the handpiece 418 through liquid line 456 and inlet 480, the conductive liquid flows through the passage 486, into passage 488 and thereafter through the plural orifices 496a–496h and onto animal 410. The spacing of these plural orifices 496a–496h is not critical. The embodiment illustrated in the figures has a relative spacing of approximately one-half inch between each respective orifice 496a–496h.

FIG. 14 also illustrates that the handpiece 418 includes plural position markings 498a–498e. As stated above, transducer 466 and protective cover 474 are positioned in slot 494. The transducer 466 and cover 474 are firmly wedged into the slot 494 and between sidewalls 500 and 502. A mid-portion of the transducer 4664 is centered on one of these respective positioning marks 498a–498e depending upon the size of the animal, before the transducer is fixed in its selected position relative to end wall 504. More specifically, the smaller the animal, the closer transducer 466 is positioned to end wall 504 of slot 494.

III. Tissue Measurements Made Using The Apparatus

The preceding paragraphs describe one embodiment of an ultrasound apparatus useful for practicing the present invention. This section discusses how to operate the apparatus, with particular reference to measuring tissue characteristics of cattle at a packing plant.

Cattle are conveyed seriatim using conveyor 500 to a tissue analysis zone 502 in a packing plant. As illustrated in FIGS. 17 and 18, the ultrasound device and computer control system described above can be used to analyze the tissue characteristics of the stunned ruminant at the packing plant. With transducer 466 transmitting continuous ultrasound signals, the operator positions handpiece 418 on the back of the animal 510. The operation of the apparatus is not critically affected by the positioning of the apparatus on the back of the animal, but its positioning is important for obtaining accurate measurement data of a desired internal tissue characteristic. Transducer 466 can be positioned between the twelfth and thirteenth rib, and typically is focused on the rib-eye muscle approximately three-quarters of the way down the muscle. Once housing 418 is correctly positioned, the operator then actuates switch 460 to dispense a predetermined amount of conductive liquid from reservoir 452 onto the back of the stunned ruminant 510. A sufficient amount of the conductive liquid is dispensed onto the ruminant 510 through line 456, passages 486 and 488, and orifices 496a–496h to obtain a clear image on a monitor (not shown). The amount of liquid dispensed is not critical, except that there must be enough to obtain a clear signal from the ultrasound transducer 466. Solely by way of example, less than about 50 milliliters, and more typically about 30 milliliters, of conductive liquid should suffice. Pump 436 can be actuated for particular predetermined lengths of time. The pump speed also can be controlled. The combination of controlling the pump speed and liquid dispensation time allows operator 514 to vary the amount of liquid dispensed upon animal 510 with each actuation of switch 460.

Positioning the transducer 466 is facilitated by monitoring the ultrasound tissue image on a monitor. If the monitor indicates that the transducer 466 is not correctly positioned, the transducer 466 can be removed from slot 494 in the handpiece 418 and repositioned. Once this is done for the first animal in a group of animals the transducer 466 likely will be correctly adjusted for all animals in the group.

Once a suitable amount of conductive liquid is dispensed, which generally takes less than about 5 seconds, and more typically about 3 seconds, operator 514 then positions transducer 466 against the animal 510 over the oil and between the twelfth and thirteenth rib of the animal 510. The transducer 466 is held steady in this position while operator 514 watches the monitor. Once a suitable image is obtained, operator 514 actuates trigger switch 462, which is electrically coupled to the ultrasound computer 428. By actuating switch 462, ultrasound computer 428 records the image and data, and calculates and records particular measurements of the animal 510. The data acquisition performed by ultrasound computer 428 is controlled by computer 424. Software is commercially available for running computer 424. This software can determine certain tissue characteristics using the ultrasound data, which includes backfat, intramuscular marbling, muscle dimensions and the location of a fat deposit, such as the rib eye fat kernel. Thus, software can be selected to perform particular measurements on each animal, and measurement data obtained can be displayed on the monitor. If insufficient or inaccurate data is received from a reading, and if the plant processing rate provides the operator time, the animal can be remeasured. This is done by pressing reset switch 464 and again pressing trigger switch 462 to take a new reading.

The information obtained for each animal 510 is downloaded into computer 424. The animal 510 is continuously conveyed by conveyor 500 along the processing line as an operator conducts tissue analysis. Once the tissue analysis is completed, then operator 514 moves the ultrasound tissue imaging and analysis device adjacent another stunned and bled ruminant for tissue imaging and analysis. Prior to applying the transducer 466 to the back of the next animal, the operator actuates reset switch 64. This clears the computer 424 and prepares it to receive new data. The process is then repeated.

FIG. 17 illustrates that the tissue analysis can be performed by a single ultrasound operator 514 using an ultrasound tissue imaging and analysis device as described above. FIG. 18 illustrates an alternative method for tissue imaging and analysis involving two operators. In this embodiment, the stunned and bled ruminant is conveyed to a first position adjacent a first operator. The first operator can either perform ultrasound analysis on the stunned cattle, with the second operator repeating the ultrasound measurements made by the first operator. Alternatively, the first and second operators can perform ultrasound analysis on every other cow so that operators 514 can match the conveying speed of conveyor 500.

Still another alternative method is to have a first operator 514 apply an ultrasound image enhancing fluid to the animal's hide at the rib-eye portion. This animal is then conveyed to a position adjacent a second operator 514. The second operator 514 then performs ultrasound tissue imaging and analysis adjacent the rib-eye portion of the ruminant 510 as the ruminant is being conveyed by conveyor 500. The second operator 514 adjusts the position of the ultrasound tissue analysis device until a good image is obtained. The ultrasound imaging and analysis device is then actuated to obtain and store tissue data.

The method of the present invention takes less than about fifteen seconds per animal to perform, typically less than about ten seconds to perform, and more typically less than about 10 seconds to perform, and more typically about 5–7 seconds to perform. The information obtained is then used to make calculations as discussed below, and is available to both the packing plant operator and the feedlot operator in real time. This is a significant improvement over the methods used prior to the present invention.

Data obtained using tissue analyses on the stunned and bled ruminant can be used to perform a variety of calculations, such as those discussed in Pratt's U.S. Pat. No. 5,673,647. For example, yield and quality can be determined. The ultrasound tissue imaging and analysis device is used to make a number of measurements, including rib eye dimensions, backfat thickness and and determinations of rib eye area and marbling. To make such measurements, the ultrasound device focuses on and locates particular tissue characteristics, including, for example, a particular fat deposit, such as the rib eye fat kernel. As soon as a good ultrasound tissue image is obtained, the measurements discussed above are made, and are recorded in a computer or on computer readable medium. Such data is correlated with the animals electronic identification tag, as well as information determined for each animal at the feedlot.

The data obtained by ultrasound tissue imaging and analysis at a packing plant is itself indicative of meat quality and/or yield, such as the backfat measurements, or can be used to make other calculations, such as yield grade. Yield grade is a scale from 1 to 5, with 1 being the most lean and 5 the least lean.

Typically, cattle backfat thickness varies from about 0.1 inch to about 1.0 inch thick. Rib eye area typically varies from about 9 square inches to about 15 square inches. Yield grade is determined by considering at least rib eye area and backfat. First though, solely with respect to backfat, backfat measuring greater than about 0.7 inch thick generally results in a yield grade of 4 or better. Average cattle have a backfat thickness ranging from about 0.4 inch to about 0.7 inch, and such backfat generally results in a yield grade of 3. Less backfat results in a yield grade of 1–2.

But, as stated above, yield grade also considers rib eye area. The USDA yield grade is determined by considering backfat thickness, rib eye area, hot carcass weight (which is determined by weighing both halves of a carcass about 15 minutes after initial processing) and pelvic, kidney and heart fat (PKH) values. Thus, for example, if a particular animal has a relatively small rib eye area and relatively thick backfat, then the animal likely will receive a yield grade of 4 or 5. And, if the animal has relatively large rib-eye area and relatively little backfat, then the animal likely would receive a yield grade of 1–2.

Marbling also can be determined using ultrasound tissue imaging and analysis of ruminants at packing plants. Marbling is determined by computer analysis of contrast differences in the ultrasound image. A quality grade is then assigned to the animal to reflect the marbling content. Marbling is specified as standard (which correlates with the least amount of marbling), select, choice and prime (prime correlates with the most amount of marbling).

Data collected at the packing plant by practicing the method of the present invention is available much sooner than if methods known prior to the present invention are used, such as waiting for and relying on government grading or area analyses of rib eye tracings. The present method makes such information available in real time to the packing plant operator, who could chose to provide such information virtually simultaneously to the feedlot operator. This accelerates payment all along the ruminant processing chain.

Moreover, the information provided by the method of the present invention appears more objective than the grading information provided by the government grading system. And, tissue characteristics are obtained prior to processing the stunned ruminant to a carcass by, amongst other things, removing the hide and perhaps simultaneously portions of backfat. Because the present system is based on collecting and analyzing repeated tissue body measurements, it is both more reliable and correlates better with the actual yield of the stunned and bled ruminant.

And, because the information concerning each animal is available sooner and generally is more accurate and reliable than the currently used subjective grading techniques, both the feedlot and packing plant operators can make use of such information for management decisions. As used herein "management decisions" depends on whether this refers to feedlot management or packing plant management. Packing plant management decisions are discussed above, and in Pratt U.S. Pat. No. 5,673,647. "Packing plant management decisions" typically refers to, for example: (a) sorting cattle; (b) further distribution; (c) pricing for either purchase or sell; (d) classifying inventory; (e) valuing inventory; and (f) selecting feedlot suppliers. It should be realized that information provided the feedlot operators can be used to change the subsequent treatment of individual animals at the feedlot, such as to increase or decrease feed, or to administer certain materials, such as growth factors. Because animal grading is done virtually simultaneously with processing of the animal at the packing plant using the method of the present invention, cattle emerging from the carcasses emerging from the processing area can be sorted into groups based on predetermined criteria, such as customer desires, yield, quality, carcass weights, size of cuts, etc. This, along with the fact that the information is available in real time, provides the packing plant operator better information faster concerning packing plant inventory. The feedlot also can be provided the information sooner, so that feedlot management decisions based on the information provided by the packing plant can be made much sooner and with more reliability than can be achieved using methods developed prior to the present invention.

EXAMPLES

The following examples are provided to illustrate certain particular features of working embodiments. The present invention should not construed to be limited by the features exemplified by such examples.

Example 1

This example describes a method for performing ultrasound tissue analysis of cattle in a packing plant prior to processing the cattle to carcasses. An electronic I.D. tag was placed on a trolley hook at a point where the rear leg of each animal was transferred from shackle to trolley. A portable tag reader was used to read the tag as it was placed on the hook, and this information was stored to establish the sequence of cattle on the trolley.

Figure 19:
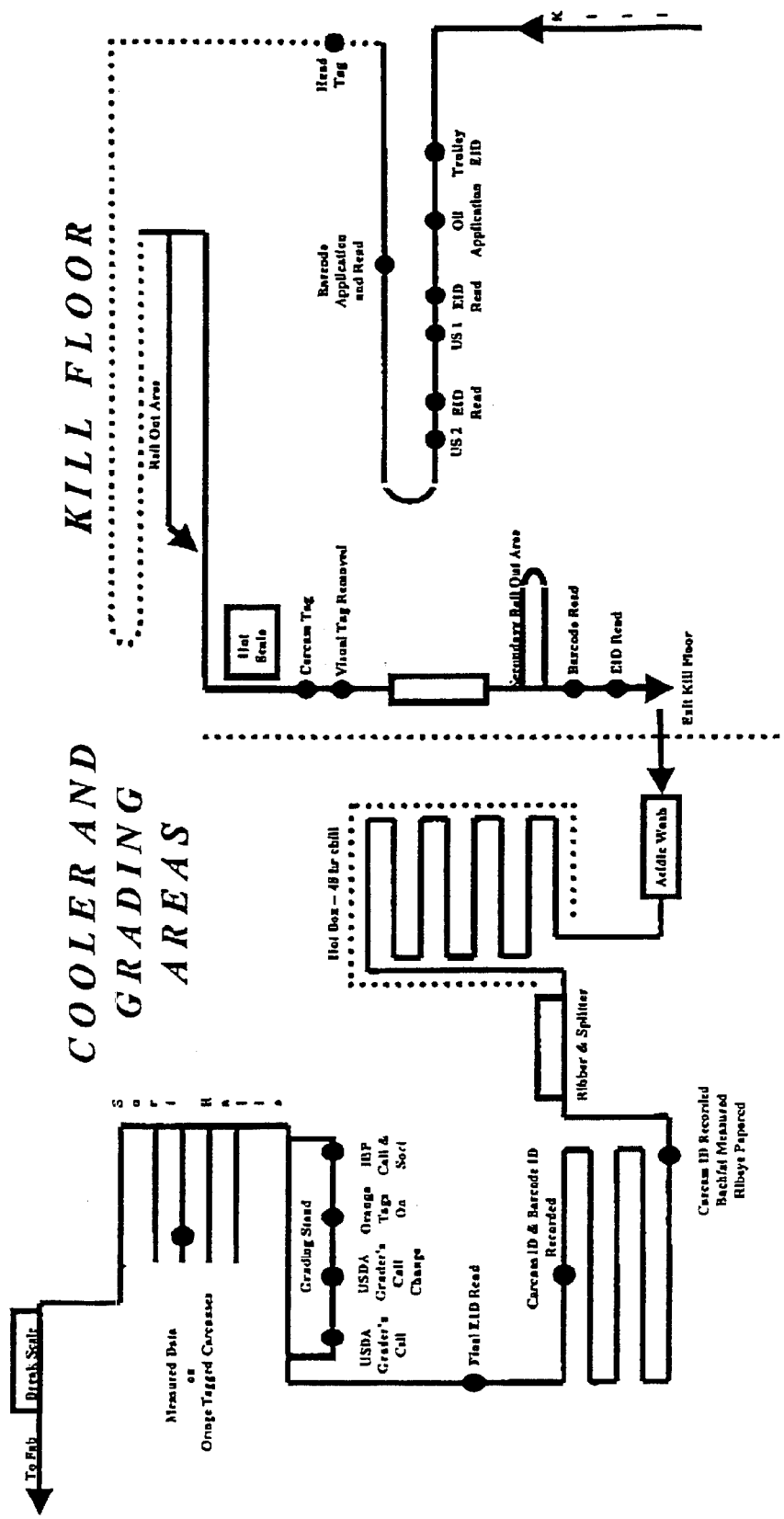
FIG. 19 is a schematic diagram illustrating the layout of a packing plant and ruminant tissue analysis locations in the packing plant.

FIG. 19 is a schematic diagram illustrating how ultrasound tissue imaging and analysis devices were positioned in a packing plant for this procedure. Just past the transfer point for transferring the stunned animal from the shackle to the trolley, the ultrasound tissue analysis zone was defined. Vegetable oil, about 18 milliliters, was applied to the hide on the left side between the $12^{th}$ and $13^{th}$ ribs before each animal was conveyed to a position adjacent an ultrasound technician.

FIG. 18 illustrates two ultrasound operators 14 performing ultrasound analysis on ruminant 10 in a packing plant. Operators 14 are illustrated as using one embodiment of an ultrasound tissue imaging and analysis system as described in more detail above comprising a switch 16, and a hand piece 18. The two successive ultrasound operators 14 used two identical computer/ultrasound systems, although it will be apparent that the two ultrasound systems need not be the same.

Following ultrasound measurement and prior to removing the head from the animal a portable tag reader was used to read the electronic identification tag which was removed from the ear of the animal. This electronic identification number was matched to the trolley sequence number and electronic identification tag on the trolley.

Ultrasound tissue analysis was performed on cattle processed at the packing plant. The tissue measurements made by the ultrasound device were stored with each animal's individual identification tag number, sequence number and trolley identification number in a computer.

A second I.D. in a form of an USDA-approved edible bar coded label was applied to the exposed brisket area. The edible label had a five-digit number printed thereon for visual reading, in addition to a bar code to be read by a hand-held reader immediately after the label was fixed to the brisket. The carcass was weighed at the hot scale. The packing plant's carcass tag was then fix to the carcass, and the weight was recorded along with the plant's carcass I.D. number on a tablet. The trolley I.D. and bar code label were read electronically to re-establish the sequence of cattle on the trolley in case some ruminants were railed-off by a USDA inspector for trimming and observation before being railed back in the moving chain. After all carcasses in the test left the packing plant for chilling, the hot carcass weight was linked to the ultrasound-derived data of backfat, rib eye area and marbling score in a file in a computer.

Yield grade, quality grade closely trimmed retail yield and pounds of each ruminant were calculated for each cattle processed using published formulas.

Example 2

This example describes a method for grading carcasses at a packing plant where objectively measured carcass data was used rather than the normal method of visual observation by graders. Immediately after the carcasses were ribbed, a numbered paper was applied to the rib eye of the left side of the carcass. The paper was removed after the rib eye impression had been made, and was traced at a later time for determining actual rib eye area on all carcasses. Immediately after the paper was removed from the rib eye, the backfat was measured with an approved preliminary-grade ruler. This measurement was recorded on a paper that was removed from that rib eye.

Each carcass was graded by a grader employing official procedures of the USDA meat grading service, and stamped accordingly with yield and quality grades. A second person from the USDA meat grading service observed the carcass as trained and then observed a computer screen displaying the yield and quality grades as calculated on day of slaughter by the ultrasound derived data plus the hot carcass weight. If the USDA grader agreed with the calculated value, he pressed the touch screen computer and a label was printed and fixed to the carcass by another worker to confirm the calculated values. If the USDA grader did not agree, he adjusted PYG, RIB EYE, and/or KPH to change the calculated yield grade and marbling score to change the quality grade. When the displayed yield grade and quality grade matched the USDA grader's evaluation, he pressed a print button on the touch screen computer and a label was printed and fixed to the carcass.

A second touch screen computer was made available to the plant grader. He could observe the carcass and compare his subjective value to that displayed on the screen. He could then make changes to PYG, KPH and rib eye to adjust the yield grade and marbling score to adjust the quality grade.

Every thirtieth carcass was railed off for measuring PYG with the official ruler and rib eye using an official grid device. Three people, two USDA meat-grading graders and one IBP selected grader, independently measured each carcass railed off. The three independent measurements were averaged to establish the official reference measurements.

The results from Examples I and II demonstrate that tissue analysis made on ruminants in packing plants can provide yield grades, rib eye areas and marbling, for example, that correlate well with those obtained by the conventional processes being used prior to the present invention. Moreover, the data provided by the tissue analysis at the packing plant is available in real time for analysis by the packing plant, the feedlot, and others in the processing line. This not only expedites payment to all persons in the processing line, but further also allows the feedlot to adjust its methods of processing ruminants, and allows the packing plant operators to better control their inventory.

The present invention has been described in accordance with working embodiments However, it will be understood that certain modifications may be made thereto without departing from the invention. I claim as my invention the preferred embodiment and all such modifications and equivalents as come within the true spirit and scope of the following claims.

I claim:

1. A method for measuring tissue characteristics of ruminants, comprising:

measuring internal tissue characteristics and/or external body measurements of ruminants at a feedlot and recording information obtained concerning each ruminant in a computer or on computer-readable medium;

stunning a ruminant at a packing plant;

conveying the ruminant to a position adjacent an operator who measures internal tissue characteristics of the ruminant;

measuring internal tissue characteristics of the ruminant using an ultrasound tissue imaging and analysis device prior to processing the ruminant to a carcass, the device comprising a dispenser for dispensing a conductive liquid, an ultrasound transducer, and a computer coupled to the transducer, the internal tissue characteristics being used to determine a characteristic selected from the group consisting of rib eye dimensions, backfat, marbling, and combinations thereof;

sorting ruminants into carcasses using predetermined criteria; and matching measurements made for each animal at the feedlot with measurements made at the packing plant.

2. The method according to claim 1 where the ruminant is a cow.

3. The method according to claim 1, further comprising conveying ruminants to the position adjacent the operator seriatim.

4. The method according to claim 1 and further comprising measuring internal tissue characteristics every 30 seconds or less.

5. The method according to claim 1 and further comprising viewing an ultrasound image on a monitor while measuring internal tissue characteristics.

* * * * *

UNITED STATES PATENT AND TRADEMARK OFFICE
CERTIFICATE OF CORRECTION

PATENT NO. : 6,579,236 B2  
DATED : June 17, 2003  
INVENTOR(S) : William C. Pratt It is certified that error appears in the above-identified patent and that said Letters Patent is hereby corrected as shown below:

Title page,  
Item [56], References Cited, OTHER PUBLICATIONS,  
"Butcher et al." reference, "Handbood" should read -- Handbook --;  
"Williams et al." reference, "form" should read -- from --;  
"Oltjen and Garrett" reference, "Rate of an Gain" should read -- Rate of Gain --; and  
"Coleman et al." reference, "Charolais Stress" should read -- Charolais Steers --.

Column 16,  
Line 32, "number 19 along" should read -- number 1-9 along --.

Signed and Sealed this

Twenty-seventh Day of December, 2005

JON W. DUDAS  
*Director of the United States Patent and Trademark Office*